(12) United States Patent
Gofman et al.

(10) Patent No.: US 9,936,903 B2
(45) Date of Patent: Apr. 10, 2018

(54) DETECTION OF CONTAMINATION AT SENSOR CONTACTS

(75) Inventors: Igor Gofman, Croton-on-Hudson, NY (US); Mu Wu, Hopewell Junction, NY (US)

(73) Assignee: WaveForm Technologies, Inc.

( * ) Notice: Subject to any disclaimer, the term of this patent is extended or adjusted under 35 U.S.C. 154(b) by 775 days.

(21) Appl. No.: 13/447,152

(22) Filed: Apr. 13, 2012

(65) Prior Publication Data

US 2013/0018597 A1    Jan. 17, 2013

Related U.S. Application Data

(60) Provisional application No. 61/475,597, filed on Apr. 14, 2011.

(51) Int. Cl.
*G01N 31/00* (2006.01)
*A61B 5/145* (2006.01)
*A61B 5/1486* (2006.01)

(52) U.S. Cl.
CPC .......... *A61B 5/145* (2013.01); *A61B 5/14532* (2013.01); *A61B 5/14865* (2013.01); *A61B 2560/0276* (2013.01)

(58) Field of Classification Search
CPC ...................................................... A61B 5/145
USPC ............................................................. 702/23
See application file for complete search history.

(56) References Cited

U.S. PATENT DOCUMENTS

| 5,481,194 A | 1/1996 | Schantz et al. |
| 5,552,713 A | 9/1996 | Rashidi |
| 5,781,024 A * | 7/1998 | Blomberg ................ A61B 5/00 204/406 |
| 6,088,608 A * | 7/2000 | Schulman .......... A61B 5/14532 600/345 |
| 7,081,195 B2 | 7/2006 | Simpson et al. |
| 2004/0147819 A1 * | 7/2004 | Caduff .................. G01N 22/00 600/316 |
| 2008/0088592 A1 | 4/2008 | Cartes |
| 2008/0219061 A1 | 9/2008 | Choi et al. |
| 2008/0278331 A1 * | 11/2008 | Hayter ................ A61B 5/0002 340/573.1 |
| 2009/0076355 A1 | 3/2009 | Reggiardo |
| 2009/0101523 A1 * | 4/2009 | Deng ................ G01N 27/3273 205/777.5 |

(Continued)

FOREIGN PATENT DOCUMENTS

WO    2009-146390    12/2009

*Primary Examiner* — Toan Le
*Assistant Examiner* — Xiuquin Sun
(74) *Attorney, Agent, or Firm* — Schwabe, Williamson & Wyatt, P.C.

(57) ABSTRACT

Embodiments herein provide detection of contamination at one or more contacts of a sensor system. The sensor system includes a sensor assembly and an electronics assembly communicatively coupled together by one or more contacts. The sensor assembly passes a sensor signal to the electronics assembly for further processing. The electronics assembly includes a detection contact for detecting contamination on or near one or more contacts of the sensor assembly and/or the electronics assembly. A switch selectively couples the detection contact to a bias voltage during a measurement mode and to a reference voltage during a detection mode, the reference voltage being different from the bias voltage. A method of contamination detection includes switching the electronics assembly between the measurement mode and the detection mode, and monitoring for a change in the output signal received by the electronics assembly.

23 Claims, 16 Drawing Sheets

(56) References Cited

U.S. PATENT DOCUMENTS

| | | | |
|---|---|---|---|
| 2009/0184688 A1* | 7/2009 | Kim | G06F 1/26 320/162 |
| 2009/0201032 A1* | 8/2009 | Burdett | G01N 27/404 324/663 |
| 2009/0240120 A1* | 9/2009 | Mensinger | A61B 5/7445 600/301 |
| 2010/0319436 A1* | 12/2010 | Sun | A61B 5/01 73/61.46 |

* cited by examiner

DETECTION OF CONTAMINATION AT SENSOR CONTACTS

CROSS REFERENCE TO RELATED APPLICATIONS

The present application claims priority to U.S. Provisional Patent Application No. 61/475,597, filed Apr. 14, 2011, entitled "DETECTION OF CONTAMINATION AT SENSOR CONTACTS," the entire disclosure of which is hereby incorporated by reference in its entirety.

TECHNICAL FIELD

Embodiments herein relate to the field of sensors, and, more specifically, to detection of contamination at sensor contacts.

BACKGROUND

Many medical sensors, such as continuous glucose monitoring (CGM) sensors include a subcutaneous sensor having one or more contacts inserted under the skin of a user to measure an analyte, such as glucose. The sensor may be worn by the user for several days. Accordingly, the sensor may be exposed to water, such as when the user is in the shower, outside in the rain, and/or participating in water sports. Contamination by water and/or other substances on or near the sensor contacts may interfere with the measurements of the sensor. However, mechanical sealing of the sensor may be challenging and may not provide an acceptable level of protection for the sensor.

BRIEF DESCRIPTION OF THE DRAWINGS

Embodiments will be readily understood by the following detailed description in conjunction with the accompanying drawings and the appended claims. Embodiments are illustrated by way of example and not by way of limitation in the figures of the accompanying drawings.

DETAILED DESCRIPTION

Figure 1A:
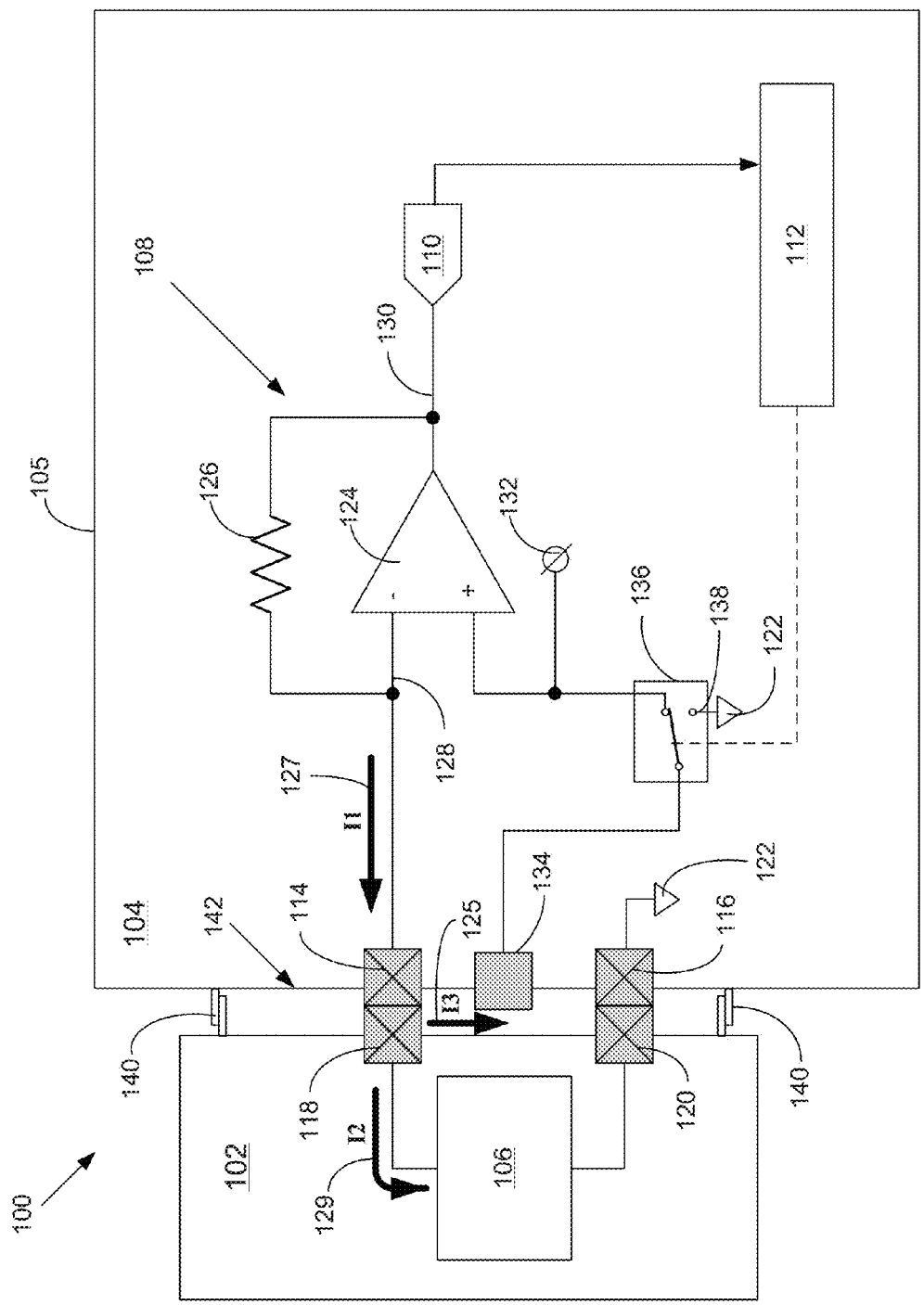
FIG. 1A illustrates a schematic diagram of an electronics assembly and sensor assembly in accordance with various aspects.

In the following detailed description, reference is made to the accompanying drawings which form a part hereof, and in which are shown by way of illustration embodiments that may be practiced. It is to be understood that other aspects and/or embodiments may be utilized and structural or logical changes may be made without departing from the scope. Therefore, the following detailed description is not to be taken in a limiting sense, and the scope is defined by the appended claims and their equivalents.

Various operations may be described as multiple discrete operations in turn, in a manner that may be helpful in understanding the disclosure; however, the order of description should not be construed to imply that these operations are order dependent.

The description may use perspective-based descriptions such as up/down, back/front, and top/bottom. Such descriptions are merely used to facilitate the discussion and are not intended to restrict the application of the disclosure.

The terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

For the purposes of the description, a phrase in the form "NB" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. The term "aspect" generally refers to features or parts/components of disclosed embodiments. Furthermore, the terms "comprising," "including," "having," and the like, as used with respect to embodiments, are synonymous, and are generally intended as "open" terms (e.g., the term "including" should be interpreted as "including but not limited to," the term "having" should be interpreted as "having at least," the term "includes" should be interpreted as "includes but is not limited to," etc.).

With respect to the use of any plural and/or singular terms herein, those having skill in the art can translate from the plural to the singular and/or from the singular to the plural as is appropriate to the context and/or application. The various singular/plural permutations may be expressly set forth herein for sake of clarity.

Methods, apparatuses, and systems for continuous monitoring of contamination at or near one or more contacts of a sensor are provided. A computing device may be endowed with one or more components of the disclosed apparatuses and/or systems and may be employed to perform one or more methods as disclosed herein.

Various aspects of embodiments herein provide methods, apparatuses, and systems for detection of contamination at one or more contacts of a sensor. Embodiments include a sensor system having a sensor assembly and an electronics assembly communicatively coupled to one another via one or more contacts. For example, in an aspect, the sensor assembly includes a sensor contact and a common return (e.g., ground) contact coupled to a sensor contact and common return contact, respectively, of the electronics assembly. The sensor assembly includes an analyte sensor that produces a sensor signal with a value (e.g., current and/or voltage) dependent on a measurement of the analyte (e.g., concentration of analyte) in a patient's body. In one aspect, the analyte sensor may be a continuous glucose monitor (CGM) that measures the concentration of glucose in the blood stream of the patient. The sensor assembly passes the sensor signal to the electronics assembly, through the sensor contacts, for further processing.

In an aspect, the electronics assembly further includes a detection contact for detecting contamination on and/or near the sensor contact and/or the common return contact of the sensor assembly and/or the electronics assembly. Contamination at or near the contacts, such as by water and/or other substances, may cause a leakage current between one or both sensor contacts and one or more of the other contacts. The leakage current may cause the sensor signal received by the electronics assembly (e.g., at the sensor contact of the electronics assembly) to be different from the sensor signal produced by the analyte sensor. Thus, the measurements of the analyte made by the electronics assembly may not accurately reflect the sensor signal.

In an aspect, the electronics assembly may be selectively placed in a measurement mode and/or a detection mode. The measurement mode may be used for normal operation of the sensor system (e.g., gathering data from the analyte sensor). In the detection mode, the electronics assembly may use the detection contact to determine whether contamination is present at one or more of the contacts. The electronics assembly may include a switch that selectively couples the detection contact to a bias voltage during a measurement mode and to a reference voltage during a detection mode. The reference voltage may be different from the bias voltage.

In an aspect, the electronics assembly may include a microprocessor (also referred to as a processor) to receive the sensor signal via the sensor contacts. The sensor signal may be amplified by an amplifier and/or digitized by an analog-to-digital converter (ADC) prior to being received by the microprocessor. Accordingly, the signal received by the microprocessor may also be referred to as the output signal of the amplifier. The microprocessor may control the switch to selectively place the electronics assembly in the measurement mode and/or the detection mode. In an aspect, the electronics assembly may take measurements of the analyte (e.g., glucose level) periodically based on the sensor signal. The microprocessor may run the detection procedure prior to each measurement.

A method of contamination detection includes switching the electronics assembly between the measurement mode and the detection mode and monitoring for a change in the sensor signal received by the microprocessor. If there is no contamination, there may be no leakage current and the sensor signal read by the microprocessor may be substantially the same whether the switch is in the measurement mode or the detection mode. If there is contamination, there may be a leakage current between the sensor contact and the detection contact. The magnitude of the leakage current will change when the switch is changed from the measurement mode to the detection mode, because of the voltage difference between the bias voltage and the reference voltage. The difference in leakage current changes the sensor signal received by the microprocessor. Accordingly, if the microprocessor detects a significant change in the sensor signal when the electronics assembly switches from the measurement mode to the detection mode (or vice versa), the microprocessor determines that a leakage current is present (e.g., due to contamination).

In an aspect, the microprocessor may compare a first value of the output signal received during the measurement mode with a second value of the output signal received during the detection mode. The comparison may include a difference between the first value and the second value (e.g., subtraction), a ratio between the first value and the second value, and/or another suitable type of comparison. If there is a change in the output signal above a threshold, e.g., a significant change, then the microprocessor may determine that a leakage current is present that is affecting with the sensor signal. The threshold may depend on several factors, such as nature of the contamination, the hardware implementation (e.g., amplifier gain), and/or actual analyte level.

The microcontroller may take one or more actions in response to the change in the sensor signal. The one or more actions may include, but are not limited to, activating an alert/alarm, generating an error code, transmitting the error code to an external device, logging the error, stopping the collection of data from the sensor, preventing the sensor data from being used in data processing, and/or taking the leakage current into account in data processing.

Alternatively, or additionally, the microcontroller may transmit the first value and the second value to a monitoring unit for further processing. The monitoring unit may compare the first value and the second value to determine whether contamination is present. The monitoring unit may then take one or more actions in response.

In an aspect, the bias voltage may also be used to bias the amplifier. Accordingly, the voltage at the sensor contact may be substantially equal to the bias voltage plus/minus an offset voltage of the amplifier. In this configuration, even if there is contamination on and/or near the contacts, the leakage current between the sensor contacts and the detection contact may be substantially eliminated (e.g., for an "ideal" amplifier) and/or relatively small (due to the relatively small offset voltage of the amplifier). This may substantially prevent the detection contact from causing changes in the sensor signal received by the electronics unit when the switch is in the measurement mode.

The reference voltage may be chosen to be substantially different from the bias voltage to facilitate detecting the leakage current. According to one implementation, the bias voltage is 0.65 Volts. In one aspect, the reference voltage is equal to the ground potential. For example, the reference voltage may be coupled with the common return contact.

The detection contact may be disposed in any suitable configuration with respect to the other contacts of the electronics assembly. In an aspect, the detection contact is located within a sealed portion where the electronics assembly is coupled to the sensor assembly. In this case, the detection contact detects contamination within the sealed portion. In an aspect, the detection contact may surround the sensor contact. For example, the detection contact may have a ring-like shape (e.g., circle, rectangle, hexagon, etc.) that surrounds the sensor contact. In this configuration, the detection contact may act as a guard ring.

In an aspect, the detection contact may be multiplexed to include one or more functions in addition to detecting contamination. For example, the detection contact may also perform the function of a battery contact. The detection contact may be coupled to a rechargeable battery of the electronics unit through a second switch. A charger may be coupled to the battery contact to charge the rechargeable battery. When the electronics assembly is in a charging mode, the second switch may couple the battery contact to the rechargeable battery. When the electronics assembly is in the monitoring mode and/or the detection mode, the second switch may couple the battery contact to a first switch similar to the switch discussed above. As discussed above, the first switch may couple the battery contact to the bias voltage when the electronics assembly is in the measurement mode, and may couple the battery contact to the reference voltage when the electronics assembly is in the detection mode. In a further aspect, the functions of the first and second switches may be combined into a single switch, such as a single-pole, triple throw switch. The first and/or second switches may include one or more transistors, such as metal-oxide-semiconductor field-effect transistors (MOSFETs).

In an aspect, the sensor assembly may include a biological sensor, such as a continuous glucose monitoring (CGM) sensor. The sensor may measure a biological parameter of a user, such as glucose level, and transmit the sensor signal to the sensor contact to be passed to the electronics assembly. A parameter of the sensor signal, such as current, voltage, duty cycle, and/or frequency, may vary depending on the level of the biological parameter measured.

In an aspect, the sensor signal may have a low-level magnitude, such as a low current. For example, the sensor signal may have a current in the range of nano to sub-nano Amperes. Accordingly, even a small leakage current may affect the sensor signal that is passed to the electronics assembly.

In an aspect, the electronics assembly may include one or more components for receiving, processing, and/or transmitting the received sensor signal, such as the amplifier, the ADC, and/or the microcontroller discussed above. The amplifier may be any suitable amplifier, such as a transimpedance amplifier and/or current integration circuit, and may include an operational amplifier. In an aspect, the bias voltage is applied to bias the amplifier to allow the sensor to operate efficiently and/or facilitate detection of the sensor signal. In a further aspect, the bias voltage may be substantially larger than the voltage of the sensor signal.

An output of the amplifier may be coupled to the ADC. The ADC may digitize the output of the amplifier and then send the digitized signal to the microcontroller. The microcontroller may perform one or more functions on the received signal, such as analyze the signal, store the signal, store data related to the signal, and/or transmit the signal and/or the data to an external device, such as a monitoring unit. In an aspect, the electronics assembly may also include a transmitter, such as a radio frequency (RF) transmitter, for transmitting signals and/or data to the monitoring unit. The microcontroller may also transmit error codes and/or data related to the detection of leakage current.

In an aspect, the sensor assembly may be used for a period of time and then replaced with another sensor assembly. In a further aspect, the same electronics assembly may be used for a longer period of time (e.g., with multiple successive sensor assemblies). Accordingly, the sensor assembly may also be referred to as the disposable sensor assembly (DSA), and the electronics assembly may also be referred to as the reusable sensor assembly (RSA).

Various aspects are described in the context of a continuous glucose monitoring (CGM) sensor, although other types of sensors may use the contamination detection system described herein.

As shown in FIGS. 1A-D, a sensor system 100 includes a sensor assembly 102 and an electronics assembly 104. Sensor assembly 102 includes a CGM sensor 106. In other embodiments, sensor 106 may be another type of biological sensor. Electronics assembly 104 includes a transimpedance amplifier 108, an analog-to-digital converter (ADC) 110, a microcontroller 112 (also referred to as processor 112), and an RF transmitter (not shown). The components of electronics assembly 104 are packaged in a hermetic housing 105 that is configured to be releasably coupled to the sensor assembly 102.

Electronics assembly 104 includes a sensor contact 114 and a common return contact 116 communicatively coupled with a sensor contact 118 and a common return contact 120 of sensor assembly 102. Common return contacts 116 and 120 are coupled to a ground potential 122. Accordingly, common return contacts 116 and 120 may also be referred to as ground contacts 116 and 120.

Some embodiments of the sensor system including the CGM sensor 106 use a current measurement method. The current measurement method is based on the glucose oxidase enzymatic reaction, which converts glucose into gluconic acid and produces hydrogen peroxide. The hydrogen peroxide liberates electrons at the contact of a polarized electrode (not shown) of the CGM sensor 106. The enzyme is enclosed in a membrane that is selective for certain blood substrates and/or reaction products. The electrode detects an electrical current (i.e., the sensor signal), which is output to the electronics assembly at sensor contact 118. The sensor signal is converted into a glucose concentration by the microcontroller 112. The sensor signal typically has a low current level, such as in the range of nano to sub-nano Amperes. Accordingly, even a small leakage current from the sensor contacts 118 and 114 may affect the accuracy of the sensor's measurements.

Additionally, the transimpedance amplifier 108 includes an operational amplifier (OA) 124 and a feedback resistor 126 coupled between an input terminal 128 and an output terminal 130 of the OA 124. The input terminal 128 of OA 124 is coupled to the sensor contact 114 to receive the sensor signal from the CGM sensor 106. Amplifier 108 is biased with a bias voltage 132 to provide a bias for the CGM sensor 106. Accordingly, the voltage at the OA input terminal 128 is substantially equal to the bias voltage 132 plus/minus an offset voltage of the OA 124. For an "ideal" OA 124, the offset voltage may be zero. The transimpedance amplifier 108 receives the sensor signal from sensor contacts 118 and 114 at OA input 128 and converts the OA input signal into an OA output signal at OA output terminal 130. The OA output signal has a voltage proportional to the current of the OA input signal. The OA output signal at OA output terminal 130 is sent to ADC 110, which digitizes the OA output signal and passes the digital signal to microcontroller 112.

If there is contamination on and/or near sensor contacts 118 and 114, a leakage current 125 flows between sensor contacts 118 and 114 and one or more of the other contacts. The leakage current 125 causes the sensor signal from sensor 106 to be different from the OA input signal received at OA input terminal 128, thereby causing inaccurate measurements of the sensor signal by microcontroller 112.

As shown in FIG. 1A, an OA input current 127 (I1) is the sum of the sensor current 129 (I2) and the leakage current 125 (I3). Therefore, in case of contamination, the OA input current 127 processed by the transimpedance amplifier 108 is:

$$I1=I2+I3$$

The OA output voltage (Vtransimpedance) at OA output terminal 130 depends on the OA input current 127 (I1), the feedback resistor 126 (Rfb), and the bias voltage 132 (Vbias):

$$V_{TRANSIMPEDANCE}=I1 \times R_{FB}+V_{BIAS}$$

Accordingly, the leakage current 125 will change the OA output voltage.

The sensor system 140 further includes a gasket 140 to seal a sealed portion 142 between the sensor assembly 102 and electronics assembly 104. The gasket 140 protects the sealed portion 142 from contamination to prevent/reduce leakage current 125. However, if the sealed portion was contaminated before the electronics assembly 104 was placed onto sensor assembly 102 and sealed, the gasket 140 will not prevent the leakage current 125. Additionally, in some circumstances, moisture may come through the gasket 140, which may cause the leakage current 125, thereby affecting the measurements.

Accordingly, the electronics assembly 104 includes a detection contact 134 to detect the presence of leakage current 125. Detection contact 134 is disposed in the sealed portion 142 of the housing 105 of electronics assembly 104. The sealed portion 142 also includes sensor contacts 114 and 118 and ground contacts 116 and 120. Detection contact 134 is coupled to a switch 136. In an aspect, switch 136 may include one or more transistors. Alternatively, or additionally, the switch 136 may include a physical switch such as a single pole, double throw switch.

The microcontroller 112 controls switch 136 to selectively couple the detection contact 134 to either the bias voltage 132 or a reference voltage 138. When the microcontroller is in a measurement mode, the switch 136 couples the detection contact 134 to the bias voltage 132. When the microcontroller 112 is in a detection mode, the switch 136 couples the detection contact 134 to the reference voltage 138. In an aspect, the reference voltage 138 is the ground potential 122. Alternatively, the reference voltage 138 may be any voltage that significantly differs from the bias voltage 132.

In the measurement mode, the voltage at the detection contact 134 is equal to the bias voltage 132 and it is the same as and/or close to the voltage at the sensor contact 114. Keeping the sensor contact 114 and detection contact 134 at substantially the same voltage reduces and/or eliminates the leakage current from the sensor contacts to the detection contact 134 in case of surface contamination during the measurement mode.

However, if the OA 124 is not an "ideal" OA, the voltage at sensor contact 114 will differ from the voltage at the detection contact by the offset voltage of OA 124. In this case, the leakage current 125 occurs between the sensor contacts 114 and 118 and the detection contact 134. The OA offset voltage is typically substantially small (e.g., on the order of microvolts), thereby creating a small leakage current 125 between the sensor contacts 114 and 118 and the detection contact 134. However, for very accurate measurements, even such a small leakage current 125 may affect the measurement of the sensor signal. Additionally, leakage current 125 may occur between the sensor contacts 114 and 118 and contacts other than the detection contact 134.

In an aspect, the switch 136 is normally in the measurement mode, with the detection contact 134 coupled to the bias voltage 132 by switch 136. The microcontroller 112 periodically initiates the detection mode, and triggers switch 136 to couple the detection contact 134 to the ground potential 122. The microcontroller 112 monitors for a change in the received sensor signal (the output signal at the OA output 130 after it is digitized by ADC 110) upon switching to the detection mode. The voltage difference between the sensor contacts 114 and/or 118 and the detection contact 134 is substantially higher in the detection mode compared to the measurement mode, since the bias voltage 132 is substantially higher than the offset voltage of the OA 124. Accordingly, a significant change in the received sensor signal when the switch 136 changes from the measurement mode to the detection mode indicates that the leakage current 125 is present (e.g., due to contamination at and/or near the contacts). The microcontroller 112 detects the leakage current by comparing a first value of the received sensor signal during the measurement mode with a second value of the received sensor signal during the detection mode. If the received sensor signal changes by more than a threshold amount, the microcontroller 112 identifies that there is a leakage current 125. In response, the microcontroller 112 takes one or more actions.

Figure 1B:
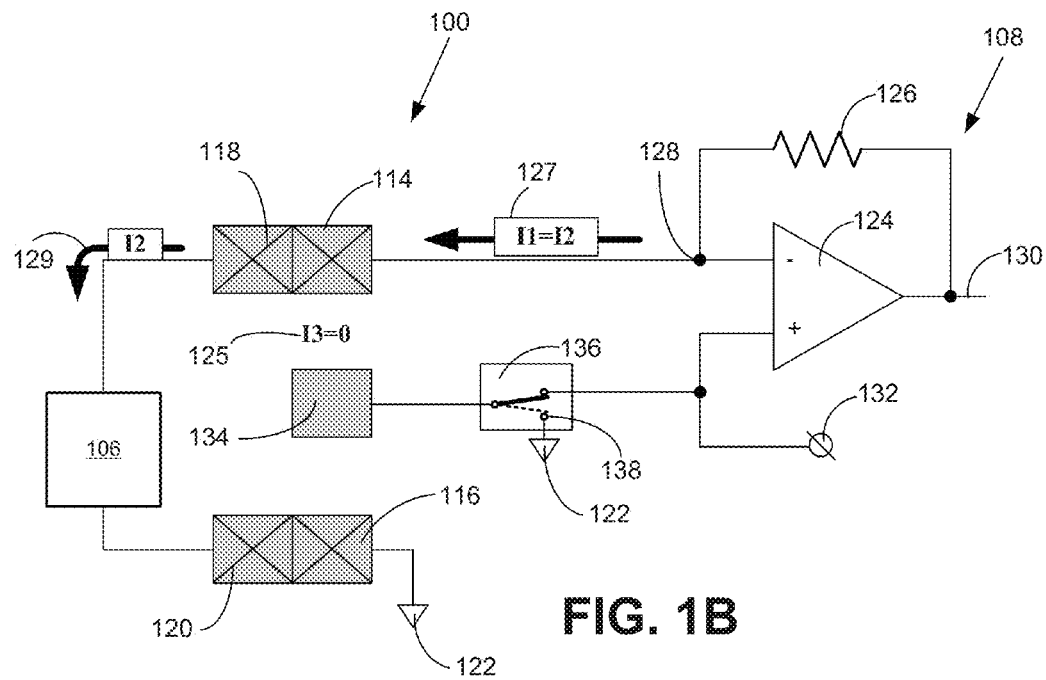
FIG. 1B illustrates a partial schematic diagram of an electronics assembly and a sensor assembly when there is no contamination, in accordance with various aspects.
Figure 1C:
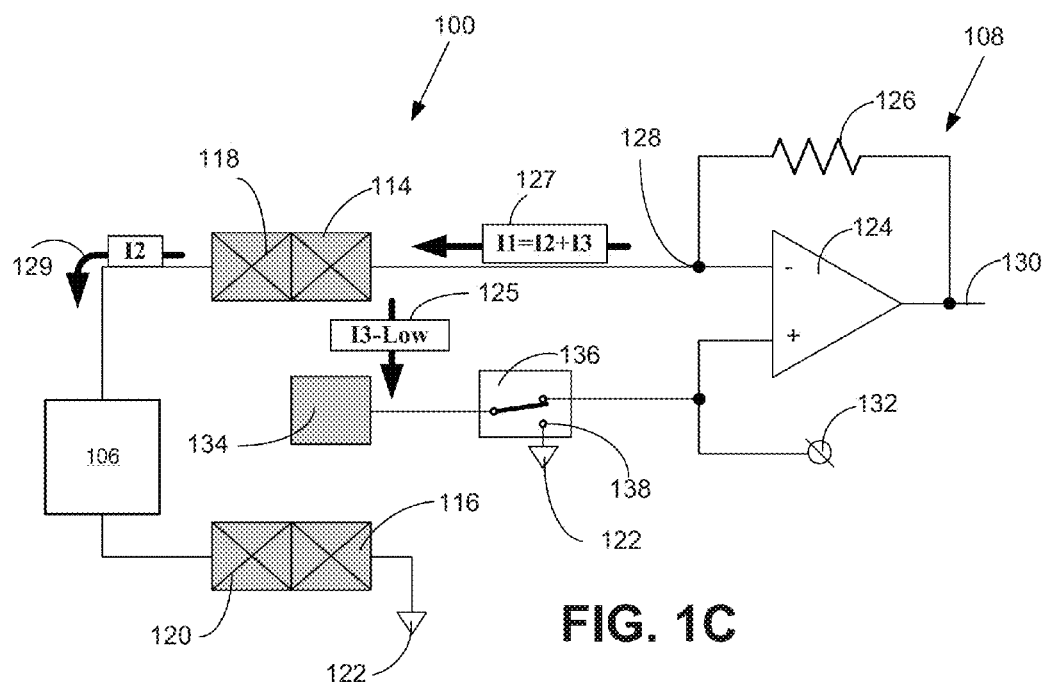
FIG. 1C illustrates a partial schematic diagram of an electronics assembly and a sensor assembly when there is contamination and the electronics assembly is in a measurement mode.
Figure 1D:
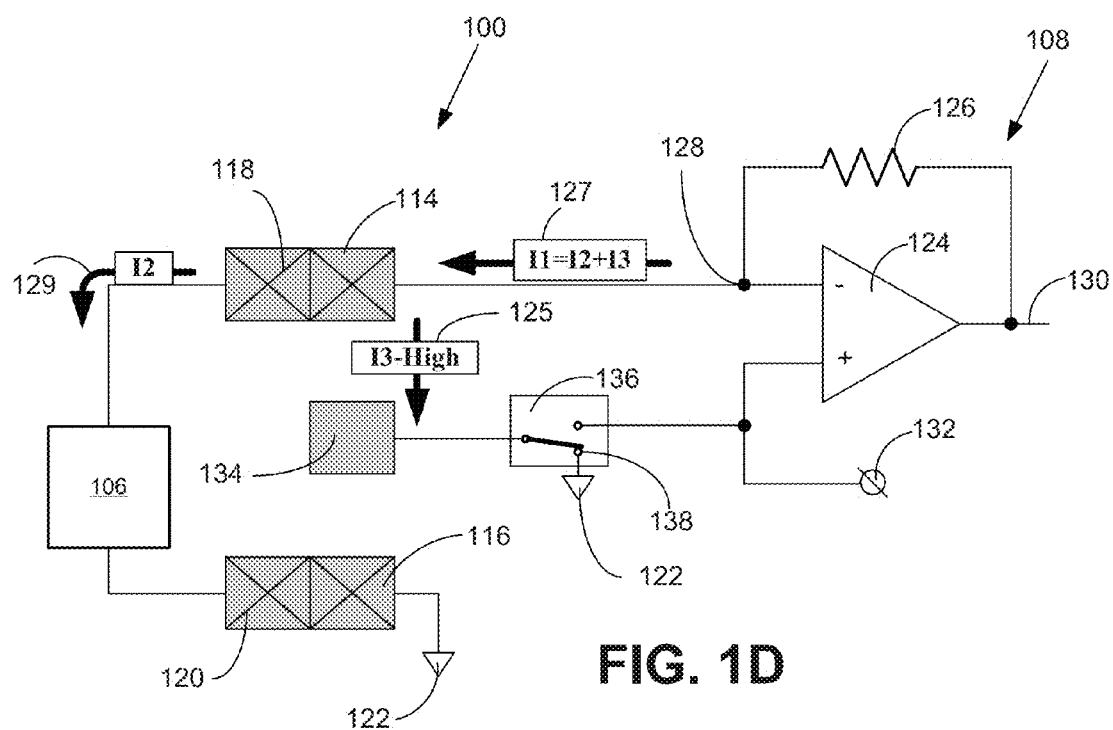
FIG. 1D illustrates a partial schematic diagram of an electronics assembly and a sensor assembly when there is contamination and the electronics assembly is in a detection mode.

To demonstrate the functionality of the electronics assembly 104 with detection contact 134, FIGS. 1B-D show partial schematic views of the sensor system 100 with illustrations of the sensor current 129 (I2), the OA input current 127 (I1), and the leakage current 125 (I3) from the sensor contacts 118 and 114 under different conditions and in different modes of operation. The leakage current 125 may flow between the sensor contacts 118 and 114 and any other contacts, such as between the sensor contacts 118 and 114 and the detection contact 134 and/or between the sensor contacts 118 and 114 and the ground contacts 116 and 120.

FIG. 1B illustrates the sensor system 100 when there is substantially no contamination on or near the contacts. In this case, the leakage current 125 will be substantially zero whether the switch 136 is coupled to the bias voltage 132 or the ground potential 122 (i.e., whether the electronics assembly 104 is in the measurement mode or the detection mode, respectively). Accordingly, the OA input current 127 will be substantially equal to the sensor current 129, providing for an accurate measurement by microcontroller 112. The output signal received by microcontroller 112 may not change substantially when the switch 136 changes from the measurement mode to the detection mode. Therefore, the microcontroller 112 will not detect a leakage current 125, and will not issue an alert. In an aspect, the microcontroller 112 takes one or more actions in response to finding there is no leakage current 125, such as storing a log of data relating to contamination detection tests, storing a log indicating that no leakage current 125 was detected, and/or transmitting a signal to the monitoring unit that no leakage current 125 was detected.

In contrast, FIGS. 1C and 1D illustrate the sensor system 100 when there is contamination at and/or near the sensor contacts 114 and 118. As shown in FIG. 1C, when the switch 136 is in the measurement mode, thereby coupling the detection contact 134 to the bias voltage 132, there is a small leakage current 125 between the sensor contacts 114 and 118 and the detection contact 134. The leakage current 125 is caused by the offset voltage of OA 124, which creates a voltage difference between the sensor contacts 114 and 118 and the detection contact 134 equal to the offset voltage. The leakage current 125 is substantially small given the small magnitude of the offset voltage. However, there may also be a component of leakage current 125 between the sensor contacts 114 and 118 and the ground contacts 116 and 120.

FIG. 1D shows sensor system 100 when there is contamination at and/or near the contacts and switch 136 is in the detection mode, thereby coupling the detection contact 134 to the ground potential 122. With switch 136 in the detection mode, the voltage difference between the sensor contacts 114 and 118 and the detection contact 134 increases substantially compared with the voltage difference in the measurement mode. The voltage at the sensor contacts 114 and 118 is equal to the bias voltage plus/minus the amplifier offset voltage, while the voltage at the detection contact 134 is equal to the ground potential 122. Accordingly, when switch 136 changes from the measurement mode to the detection mode, leakage current 125 increases substantially. The change in leakage current 125 causes a corresponding change in the OA output signal received by the microcontroller 112. Therefore, the microcontroller 112 identifies the presence of the leakage current 125 by switching from the measurement mode to the detection mode and monitoring for a change in the received OA output signal. If the OA output signal changes above the threshold amount, then the microcontroller 112 identifies that leakage current 125 is present in sufficient quantity to interfere with the sensor measurement. In response, the microcontroller 112 takes an action, such as activating an alert, logging the error, and/or transmitting an error code.

Figure 2A:
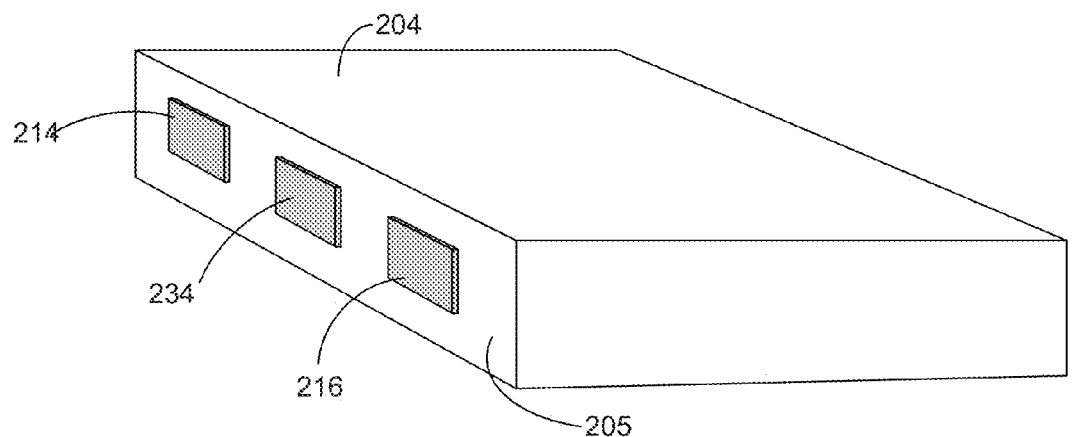
FIG. 2A illustrates an electronics assembly in accordance with various aspects.
Figure 2B:
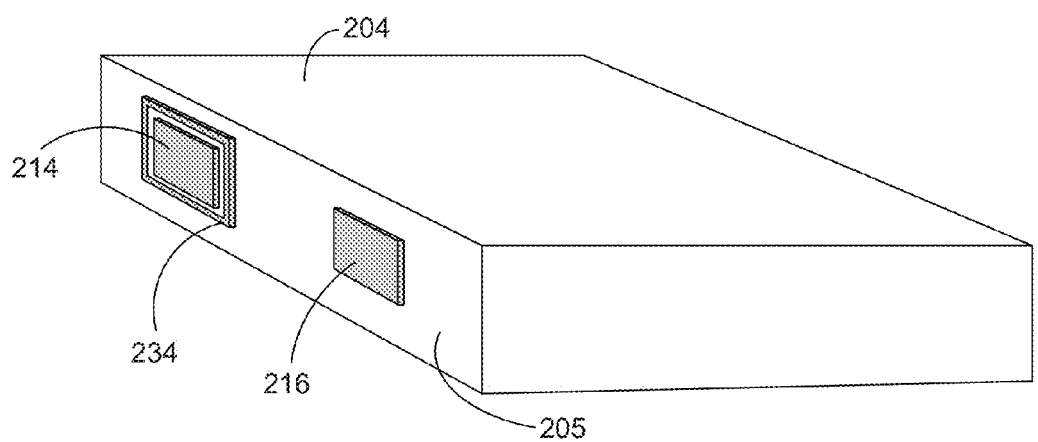
FIG. 2B illustrates an electronics assembly in accordance with various aspects.

FIGS. 2A-B show simplified examples of the configuration of the detection contact 234 on the electronics assembly 204 in relation to the sensor contact 214 and the common return (ground) contact 216. As shown in FIG. 2A, the detection contact 234 is disposed between the sensor contact 214 and the common return contact 216 on the housing 205 of electronics assembly 204. The detection contact 234 disposed between the sensor contact 214 and the common return contact 216 acts as a guard pad to reduce and/or eliminate leakage current from flowing between sensor contact 214 and common return contact 216. In some cases, leakage current instead flows between detection contact 234 and common return contact 216, but this will not affect the measurement of the sensor signal.

In an alternative configuration, the detection contact 234 may surround the sensor contact 214, as shown in FIG. 2B. In this case, the detection contact 234 may act as a guard ring. As such, the detection contact 234 reduces and/or eliminates leakage current from flowing between sensor contact 214 and common return contact 216. Leakage current may instead flow between detection contact 234 and common return contact 216.

In configurations where detection contact 234 is configured as a guard ring, the detection contact 234 may surround any one or more of the contacts. For example, in an aspect, the detection contact 234 may surround the sensor contact 214 and the common return contact 216. It will be apparent that numerous other configurations for the detection contact are contemplated.

In an aspect, the electronics assembly may include one or more additional contacts apart from the sensor contact and the common return contact, such as a battery contact, an enable contact, and/or another contact. In a further aspect, the detection contact may be multiplexed with one or more of the additional contacts to perform multiple functions. The leakage current may occur between the sensor contact and any other contact. Therefore, the contamination detection method may work using any configuration of the detection contact.

Figure 3A:
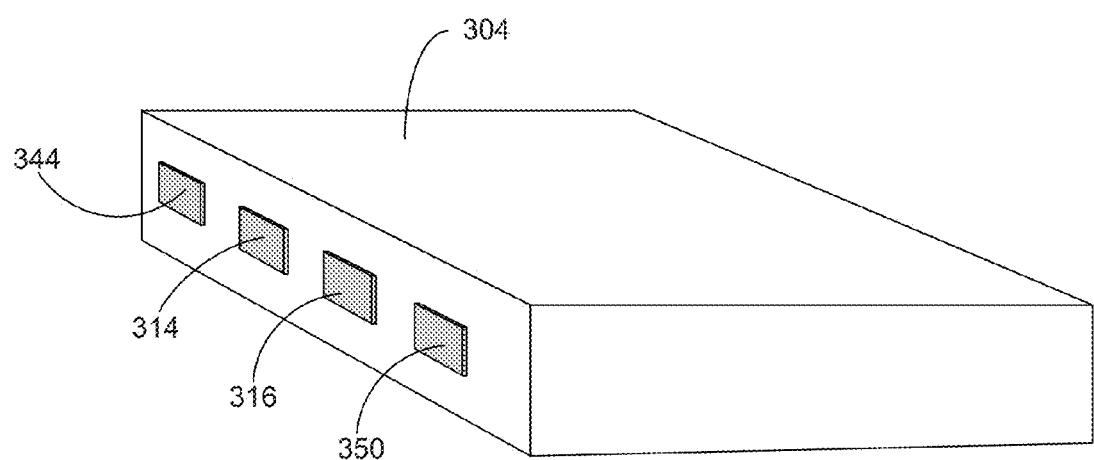
FIG. 3A illustrates an electronics assembly in accordance with various aspects.
Figure 3B:
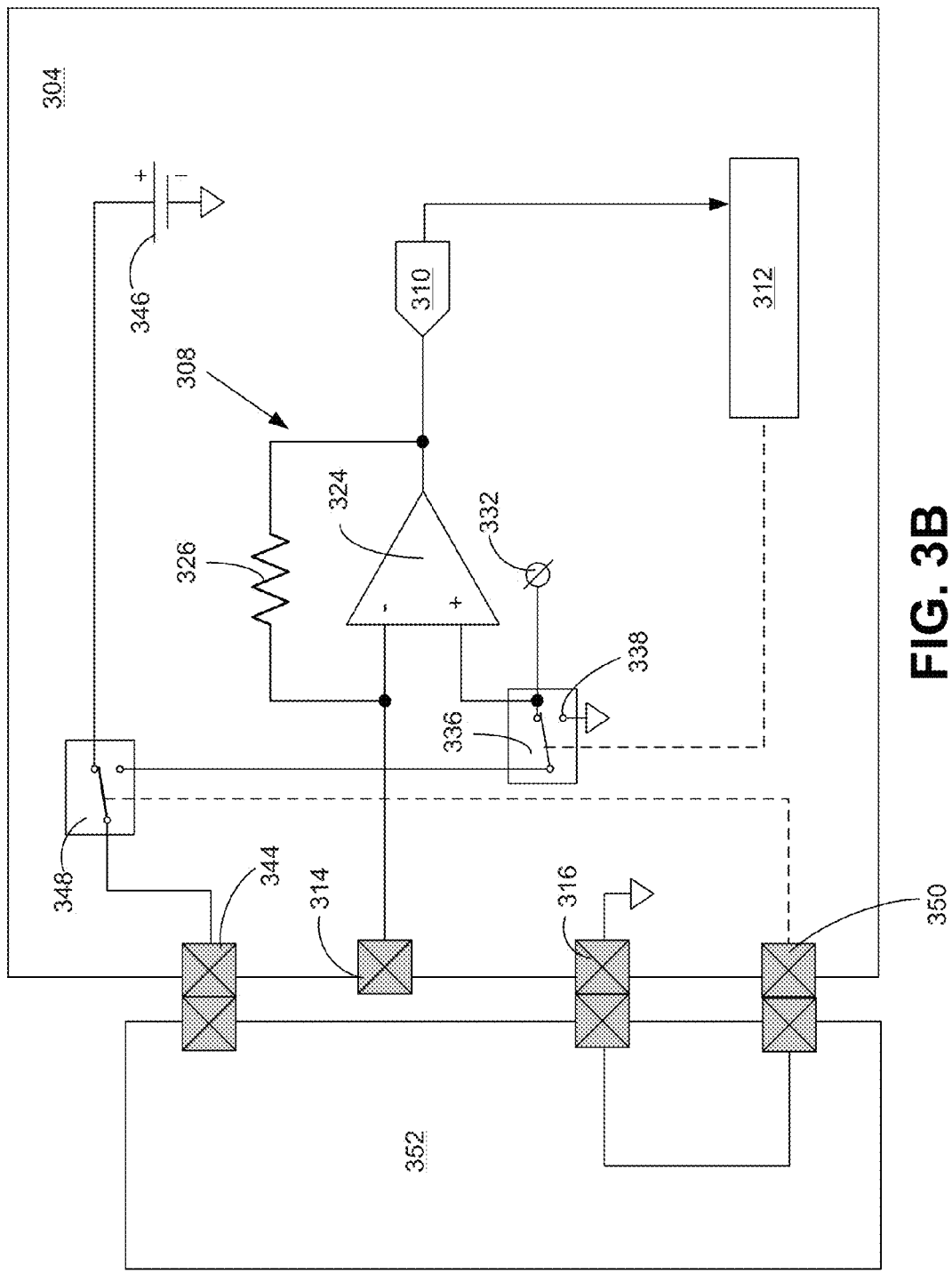
FIG. 3B illustrates a charger coupled with an electronics assembly when the electronics assembly is in a charging mode, in accordance with various aspects.
Figure 3C:
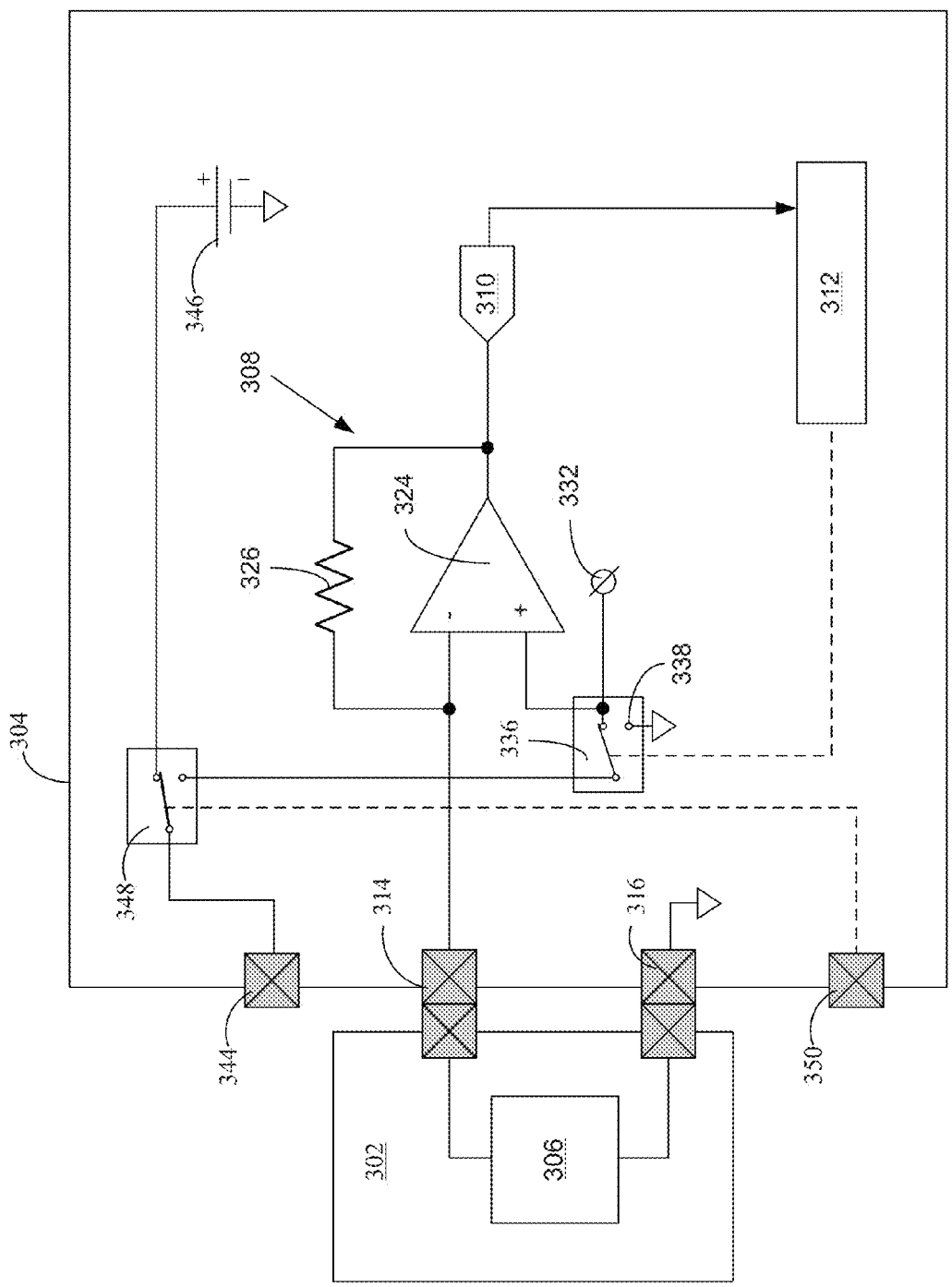
FIG. 3C illustrates a schematic diagram of an electronics assembly and a sensor assembly when the electronics assembly is in a measurement mode.

For example, FIGS. 3A-C illustrate an electronics assembly 304 with a multiplexed detection contact 344 that is multiplexed to include the functions of a battery contact. Accordingly, the detection contact 344 may also be referred to as battery contact 344. The detection contact 344 may be selectively coupled to a rechargeable battery 346 of the electronics unit through a second switch 348. The electronics assembly 304 further includes a sensor contact 314, a common return (ground) contact 316, and an enable contact 350. Sensor contact 314 is coupled to an input 328 of a transimpedance amplifier 308 having an OA 324 and a feedback resistor 326. An output 330 of transimpedance amplifier 308 is coupled to an ADC 310. ADC 310 is coupled to a microcontroller 312.

As shown in FIG. 3B, a charger 352 is coupled to the multiplexed detection contact 344 to charge the rechargeable battery 346. The electronics assembly 304 enters a charging mode when the charger 352 is coupled to the detection contact 344. The charger 352 provide a control signal (also referred to as an enable signal), such as a low signal, on the enable contact 350. The control signal is sent to the second switch 348, causing the second switch 348 to couple the detection contact 344 to the rechargeable battery 346.

Conversely, when the electronics assembly 304 is coupled with a sensor assembly 302 having an analyte sensor 306, as shown in FIG. 3C, the enable contact 350 is floating (e.g., is not receiving the control signal), causing the second switch 348 to couple the detection contact 344 to a first switch 336. Similar to the switch 132 discussed above with reference to FIGS. 1A-D, the first switch 336 couples the detection contact 344 to a bias voltage 332 when the electronics assembly 304 is in the measurement mode (as shown in FIG. 3C), and couples the detection contact 344 to a reference voltage 338 when the electronics assembly 304 is in the detection mode.

Thus, the detection contact 344 is used to charge the internal battery 346 of the electronics assembly 304 in the charging mode and used to detect a leakage current when in the measurement mode and/or detection mode. This allows the detection function to be integrated into a battery contact of the electronics assembly, eliminating the need for an additional contact to be used as the detection contact.

Additionally, in the event of contact contamination, this multiplexed approach may reduce and/or eliminate leakage current between the sensor contacts and the battery contact when the electronics assembly is in the measurement mode. When the battery contact is coupled to the battery, there is a relatively large voltage difference between the battery contact and the sensor contacts. However, by multiplexing the battery contact with the detection contact, the battery contact is disconnected from the battery during the measurement mode and instead connected to the bias voltage. Accordingly, the battery contact and sensor contacts are at substantially similar voltage potentials, thereby reducing and/or eliminating the leakage current between them.

In an aspect, one or more of the detection contact 344, sensor contact 314, common return contact 316, and/or enable contact 350 may be disposed within a sealed portion (not shown) of the housing of the electronics assembly 304. The sealed portion may be sealed from outside elements by a gasket (not shown) or other mechanism that couples the electronics assembly 304 to the sensor assembly 302. In an aspect, the detection contact 344 and/or enable contact 350 is disposed on the electronics assembly 304 within the outer dimensions of the sensor assembly 302 such that the detection contact 344 is located in the sealed portion.

In another aspect, one or more of the contacts is disposed within a guard ring on the electronics assembly 304. In an aspect, the detection contact 344 is configured as a guard ring and surrounds one or more of the other contacts, such as the sensor contact 314, common return contact 316, and/or enable contact 350.

EXPERIMENTAL RESULTS

Various experiments were performed to demonstrate the source of leakage current and the benefits of the detection contact for detecting and/or reducing the leakage current. The experiments were performed using an electronics assembly (referred to below as the RSA) having a battery contact multiplexed to perform contamination detection.

BACKGROUND

The embodiment of the RSA used in the experiments eliminated a huge voltage difference between battery and sensor contacts. Originally, the voltage difference Λ was:

$$\Lambda = V_{BAT\_MAX} - 0.65V = 4.2V - 0.65V = 3.55V$$

where $V_{BAT\_MAX}$ is the maximum battery voltage.

Figure 4:
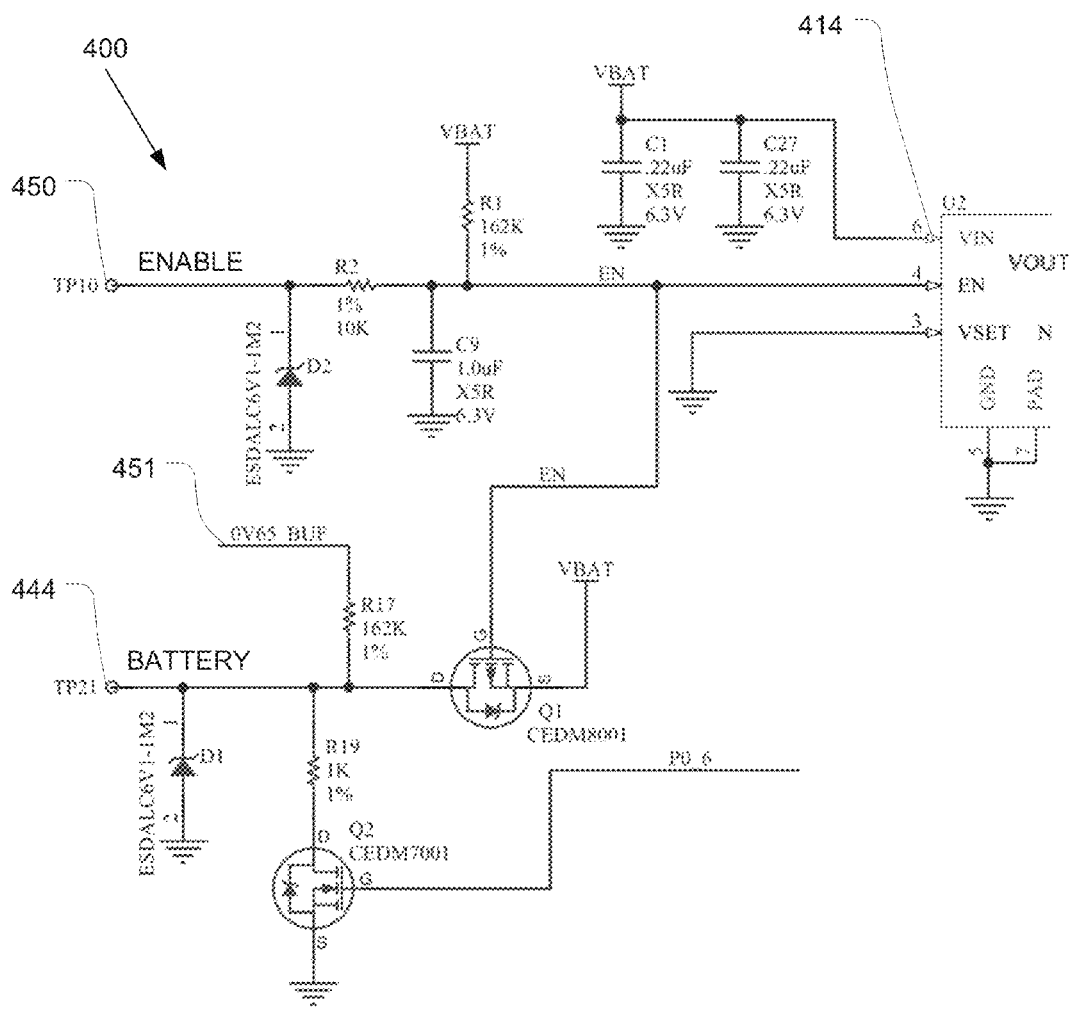
FIG. 4 illustrates a schematic diagram of an electronics assembly in accordance with various aspects.

FIG. 4 shows a schematic of an RSA 400. RSA 400 includes a battery/detection contact 444, an enable contact 450, and switches Q1 and Q2. Switches Q1 and Q2 are both MOSFET switches. Switch Q1 is similar to the second switch 348 in FIGS. 3A-3C for selectively coupling the battery contact 444 to a battery for charging the battery during the charging mode. Switch Q2 is similar to the first switch 336 in FIGS. 3A-3C for selectively switching the RSA 400 between the measurement mode and the detection mode. During normal operation of RSA 400, the MOSFET Q1 is OFF. Therefore, the battery contact 444 is disconnected from the battery during normal operation. At the same time, the battery contact 444 is biased with a pull-up resistor R17 to a +0.65V buffer 451. Accordingly, the battery contact and sensor contact 414 (VIN) are at the same potential. Theoretically, at these conditions there should be no leakage current between these contacts.

Four baseline tests were performed with three RSA units to prove this concept. The tests are explained below and followed by the results.

Test Setup

Test 1

Figure 5:
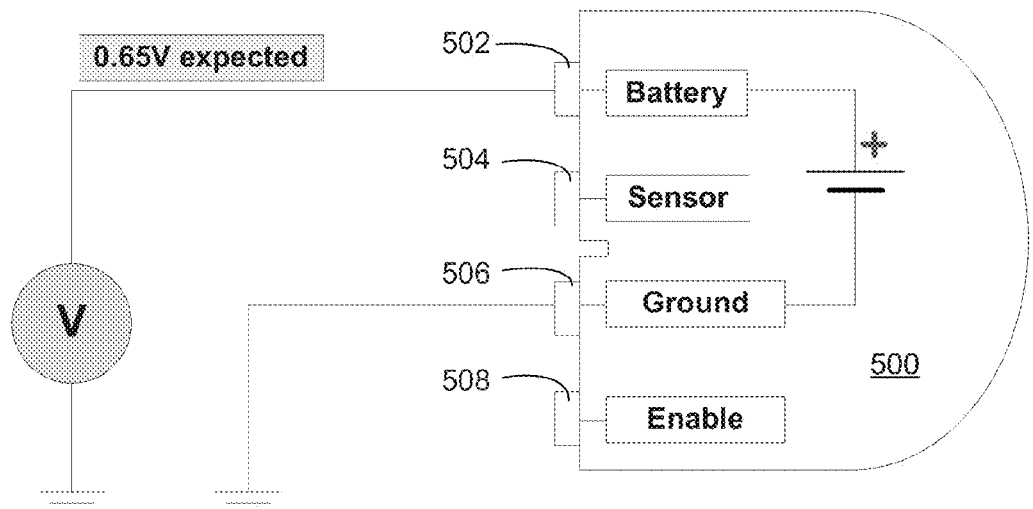
FIGS. 5-8 illustrate experimental setups for Tests 1-4, respectively, in accordance with various aspects.

The experimental setup for Test 1 on an RSA 500 is shown in FIG. 5. RSA 500 includes a battery/detection contact 502, a sensor contact 504, a ground contact 506, and an enable contact 508. In Test 1, the voltage from the battery/detection contact 502 to ground is measured during the measurement mode of RSA 500. Test 1 shows how well the RSA battery is isolated from the RSA contact. In theory, the voltage should be close to the BIAS voltage (0.65V).

Test 2

Figure 6:
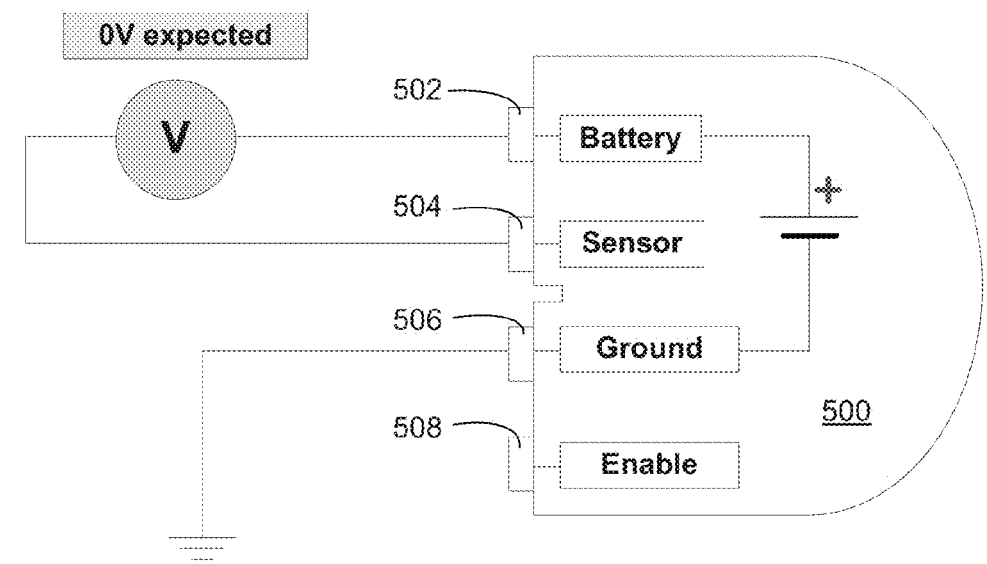

The experimental setup for Test 2 is shown in FIG. 6. Test 2 measures the voltage difference from the battery/detection contact 502 to the sensor contact 504 during the measurement mode. If RSA 500 is contaminated, this voltage may potentially cause the leakage current from the battery/detection contact 502. The target voltage difference is about zero Volts.

Test 3

Figure 7:
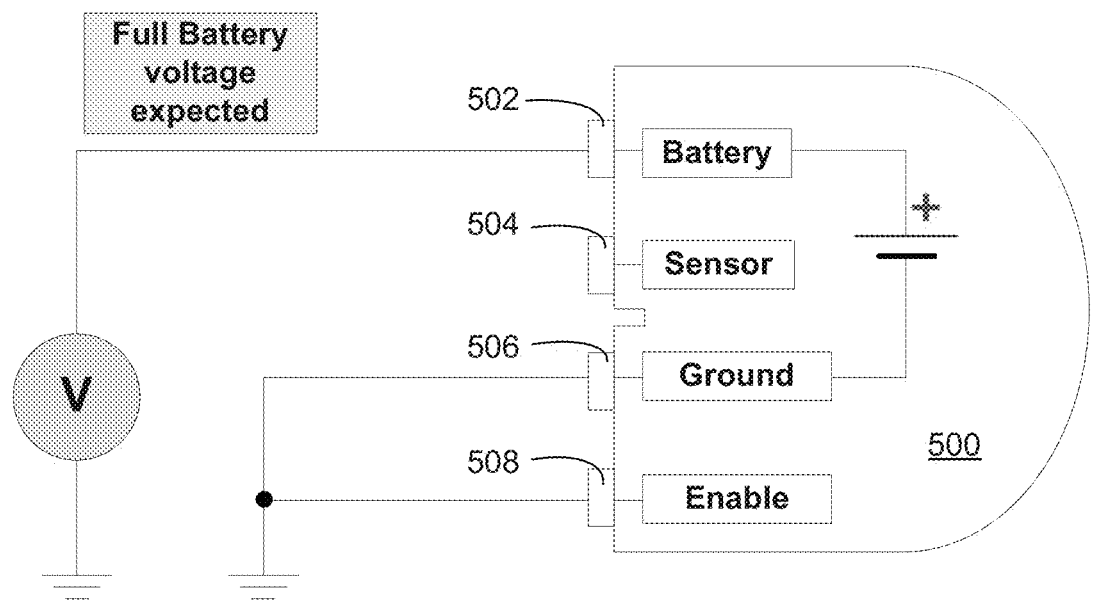

The experimental setup for Test 3 is shown in FIG. 7. Test 3 measures the voltage from battery/detection contact 502 to ground in charging mode. Test 3 demonstrates the quality and controllability of the internal MOSFET switch that will be on when ENABLE contact 508 is pulled down. In theory, the voltmeter will show a full battery voltage.

Test 4

Figure 8:
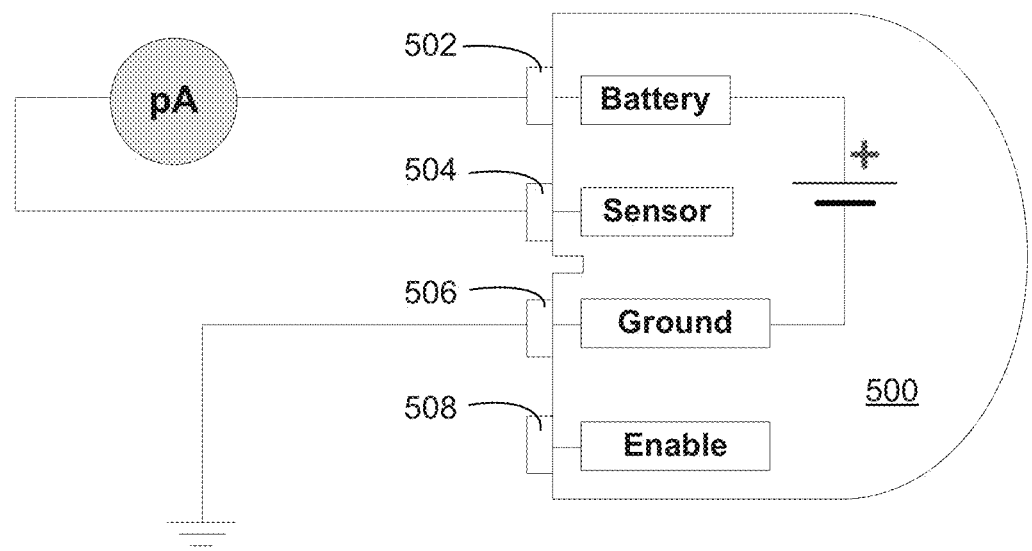

The experimental setup for Test 4 is shown in FIG. 8. Test 4 measures the leakage current between the battery/detection contact 502 and the sensor contact 504 with and without contamination. Test 4 shows the maximum theoretical leakage in case of contamination from the battery/detection contact 502. The ideal number is no more than a few pA.

Test Results

The results of Tests 1-4 for three different RSAs are shown in Table 1 below.

TABLE 1

| TEST | Test Description | RSA 1 | RSA 2 | RSA 3 |
|---|---|---|---|---|
| TEST 1 | Battery to Ground Voltage | 0.6384 V | 0.6377 V | 0.6350 V |
| TEST 2 | Battery to Sensor Voltage | 0.0 mV | 0.0 mV | 0.0 mV |
| TEST 3 | Battery to Ground Voltage in Charge mode | 4.154 V 4.154 V | 4.101 V 4.101 V | 4.120 V 4.120 V |
| TEST 4 | Battery to Sensor Leakage | 1-10 pA | 1-5 pA | 1-10 pA |

As shown in Table 1, all three RSAs have virtually no leakage between battery and sensor contacts.

However, despite the good test result, the voltage between battery contact 502 and sensor contact 504 is not always zero. Rather, the voltage between the battery contact 502 and sensor contact 504 is equal to the offset voltage of the operational amplifier in RSA 500. According to the datasheet of the operational amplifier used, its maximum offset voltage is ±150 µN. In comparison to the previous RSA approach, this voltage difference is small (±150 µV vs. 3.55V for old RSA). However, even this voltage difference may create some additional leakage that can affect the sensor current measurement.

Figure 9:
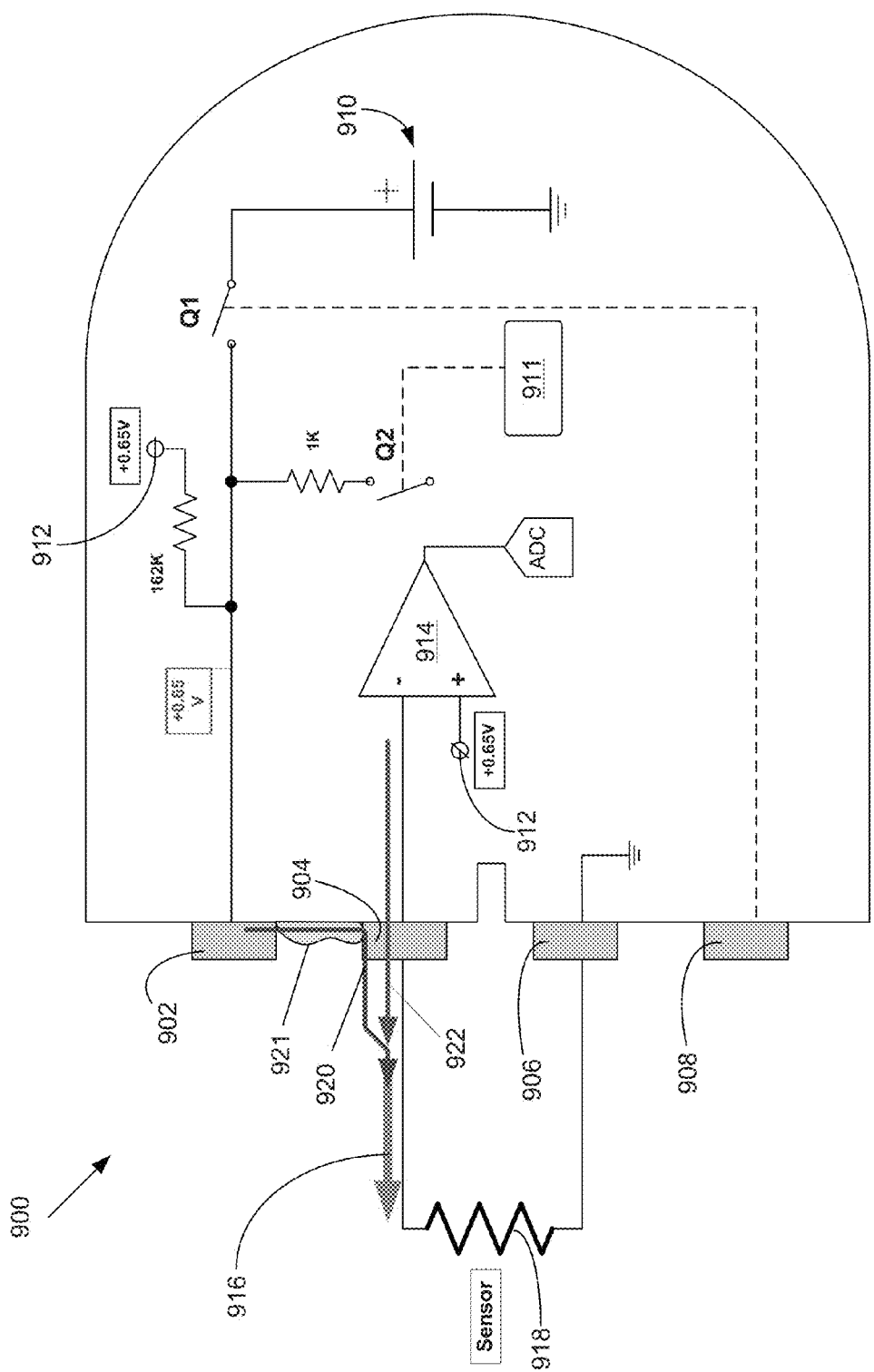
FIG. 9 illustrates a leakage current in an electronics assembly in a measurement mode, in accordance with various aspects.
Figure 10:
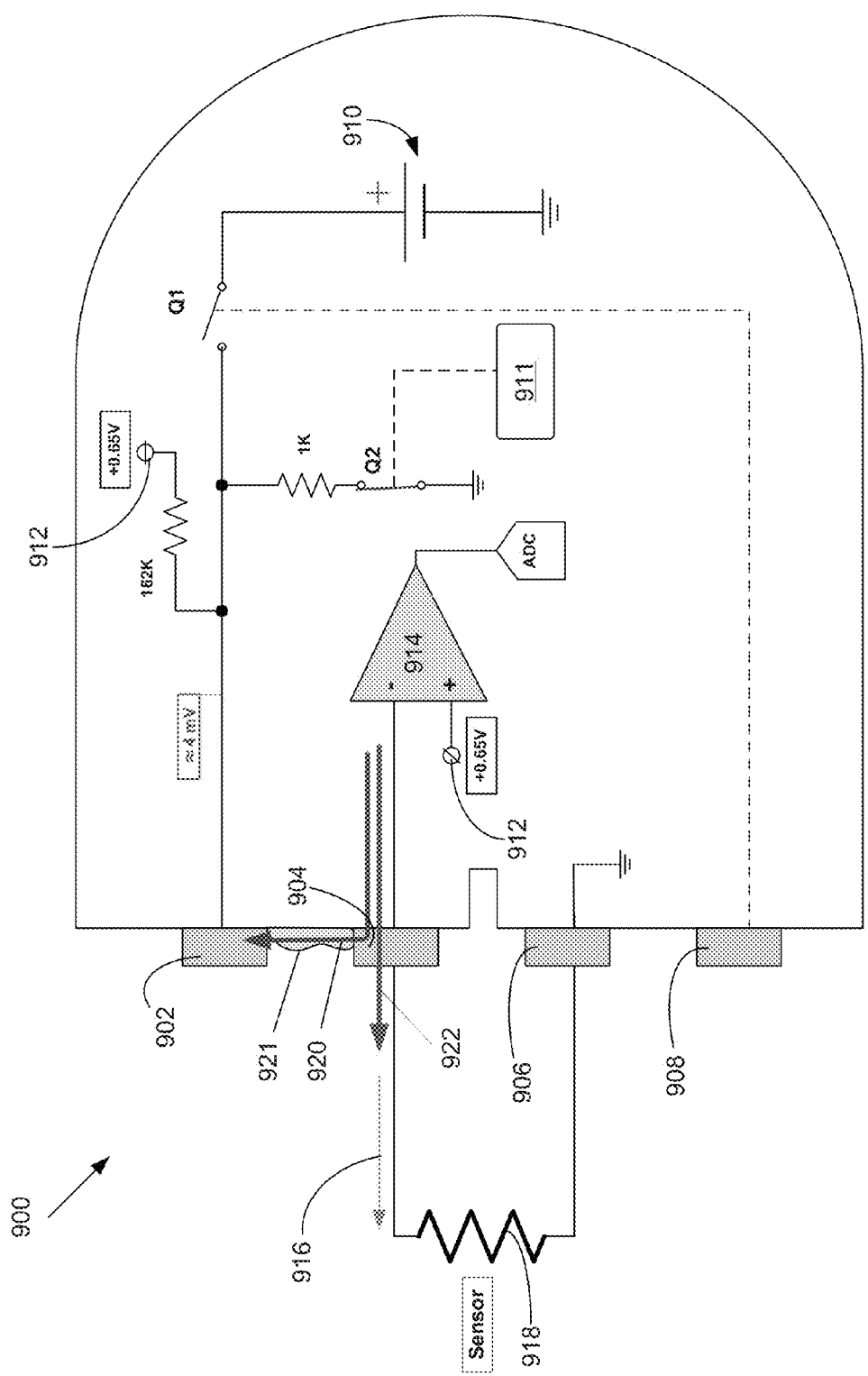
FIG. 10 illustrates a leakage current in an electronics assembly in a detection mode, in accordance with various aspects.

FIGS. 9 and 10 show an RSA 900 with various currents illustrated to show how contamination may affect the measurement. RSA 900 includes a battery contact 902, sensor contact 904, ground contact 906, and enable contact 908. Switch Q1 (similar to the second switch 348 in FIGS. 3A-3C) is controlled by the enable contact 908 and selectively couples the battery contact 902 to a battery 910 for charging during a charging mode. Switch Q2 (similar to the first switch 336 in FIGS. 3A-3C) is controlled by a microprocessor 911 and selectively couples the battery contact to ground during a detection mode. In a measurement mode, both switches Q1 and Q2 are off, and the battery contact is at a bias voltage 912 (e.g., +0.65V).

FIG. 9 illustrates the RSA 900 in the measurement mode with both switches Q1 and Q2 off. A transimpedance amplifier 914 is biased with the bias voltage 912 to keep the voltage at the sensor contact 904 substantially the same as the battery contact 902 (+0.65V). Accordingly, a total sensor current 916 depends only on the resistance of sensor 918, with a leakage current 920 caused by contamination 921. According to the 1$^{st}$ Kirchhoff's Law, the total sensor current 916 is the sum of an amplifier input current 922 (e.g., bias current 922 in FIG. 9) and the leakage current 920. Accordingly, the input current 922 of the transimpedance amplifier 914 is affected by the leakage current 920 and the measurement may be incorrect.

FIG. 10 illustrates the RSA 900 in the detection mode with Q1 off and Q2 on. In a detection algorithm, the sensor measurement may be performed in two stages. A first measurement is performed when Q2 is OFF (as shown in FIG. 9). The second measurement is performed when Q2 is ON (as shown in FIG. 10). In the second stage, the voltage at the battery contact 902 drops down to about +4 mV. The voltage at the sensor contact remains +0.65V. Without a leakage current 920, both measurements will be substantially the same.

However, if a surface of the RSA 900 is contaminated, the leakage current 920 from the sensor contact (+0.65V) will flow to the battery contact (+4 mV) during the detection mode, as shown in FIG. 10. The total input current 922 of the transimpedance amplifier 914 will rise, causing the output voltage of the amplifier 914 to also rise. By comparing two sequential results, the existence or absence of contamination (and thereby leakage current 920) is detected.

Simulation of Contamination Detection in TINA-TI

Figure 11:
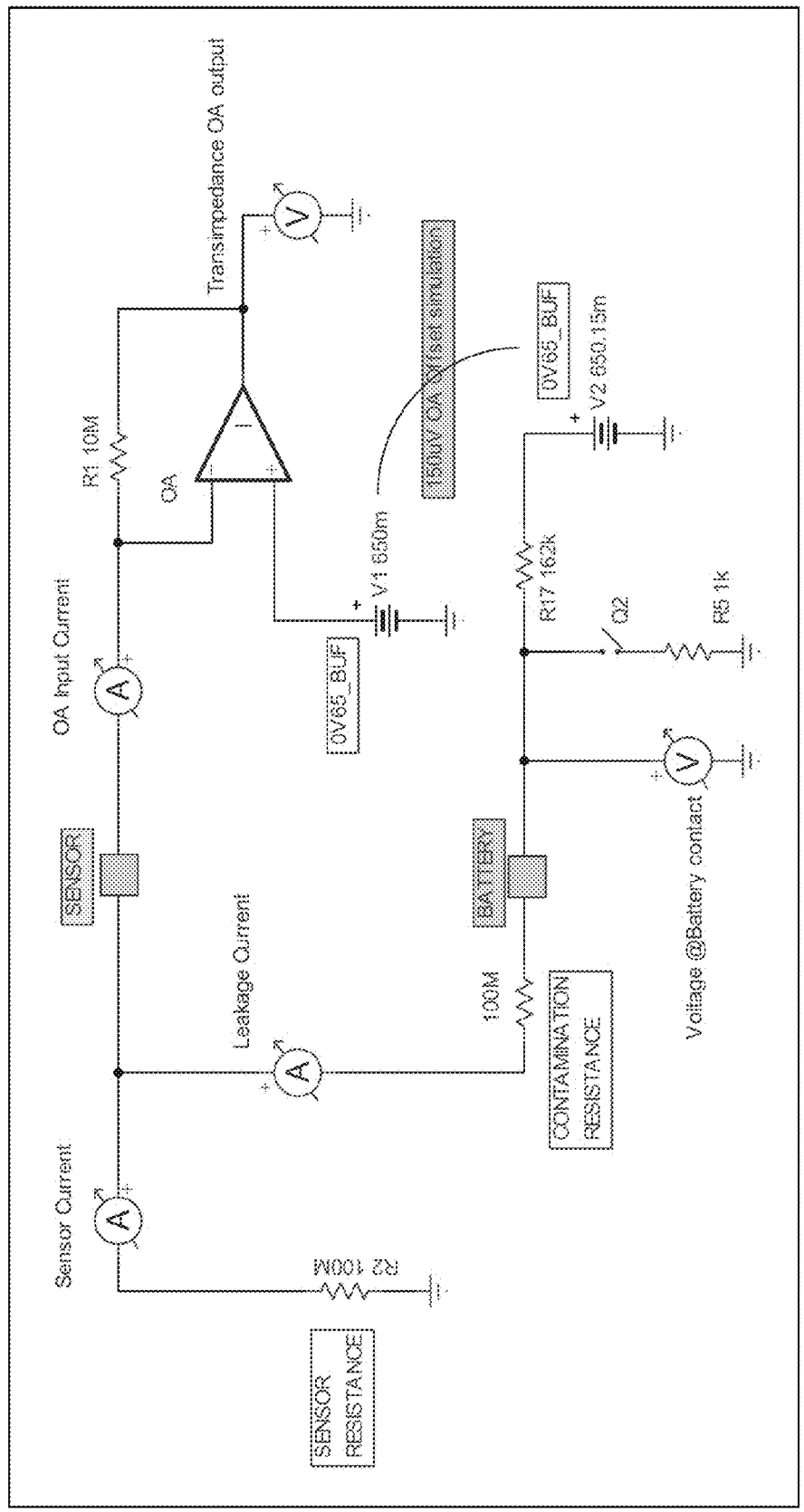
FIG. 11 illustrates a schematic diagram used to simulate an electronics assembly, in accordance with various aspects.
Figure 12A:
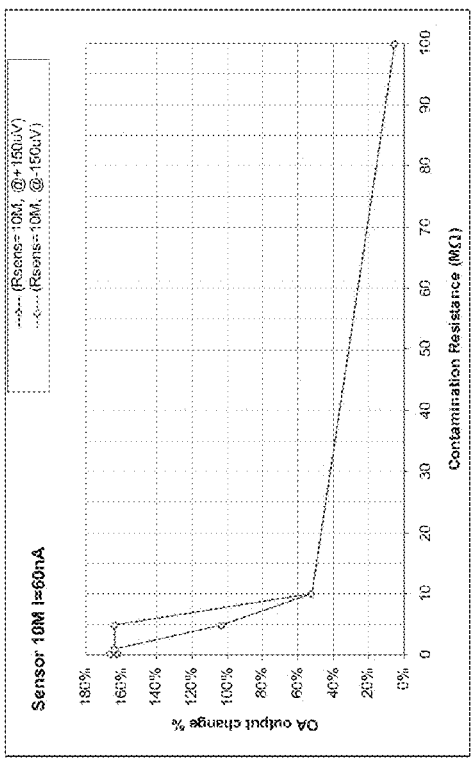
FIGS. 12A-D illustrate test results of a simulation of an electronics assembly, in accordance with various aspects.
Figure 12B:
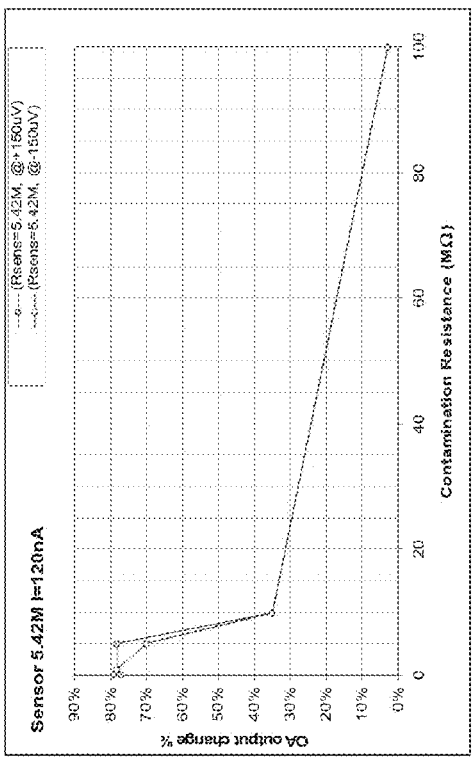
Figure 12C:
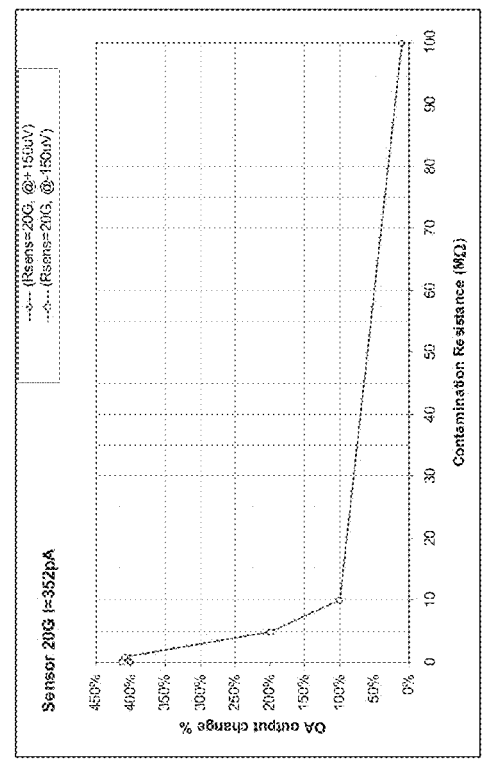
Figure 12D:
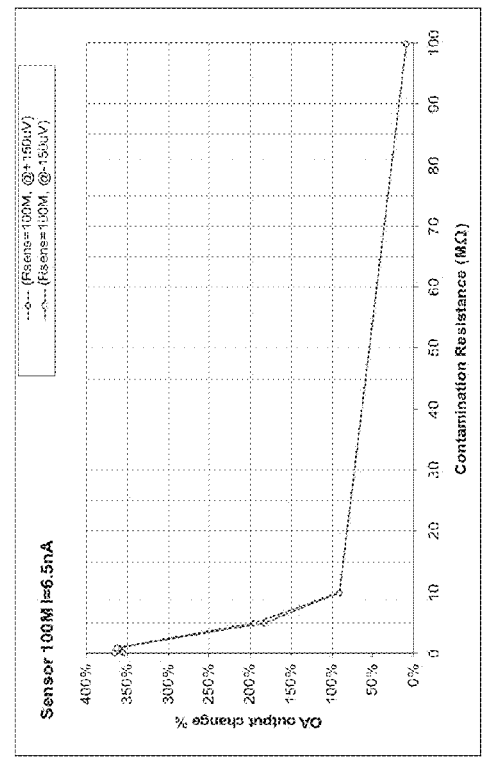

The contamination detection procedure discussed above was simulated in TINA-TI. The schematic used for the simulation is shown in FIG. 11. The results from the simulation are shown in Table 2.

tively) at different Sensor Resistance and contamination levels. As it was expected, the voltage change is more significant at a lower contamination resistance. The worst detection case is the highest sensor current and the lowest leakage. For instance, at 120 nA sensor current (5.42M—lowest sensor resistance) and 100M Contamination Resistance, the voltage changes by only about 3%. However, that change may be enough to detect the leakage current. The permissible leakage current may be determined based on a number of factors. The simulations shown in FIGS. 12A-D were done for the contamination resistance range of 100 kΩ-20 GΩ. For the values below 100 kΩ, the detection is even easier because the voltage may swing by more than 77% as shown.

Contamination Detection Algorithms

Figure 13:
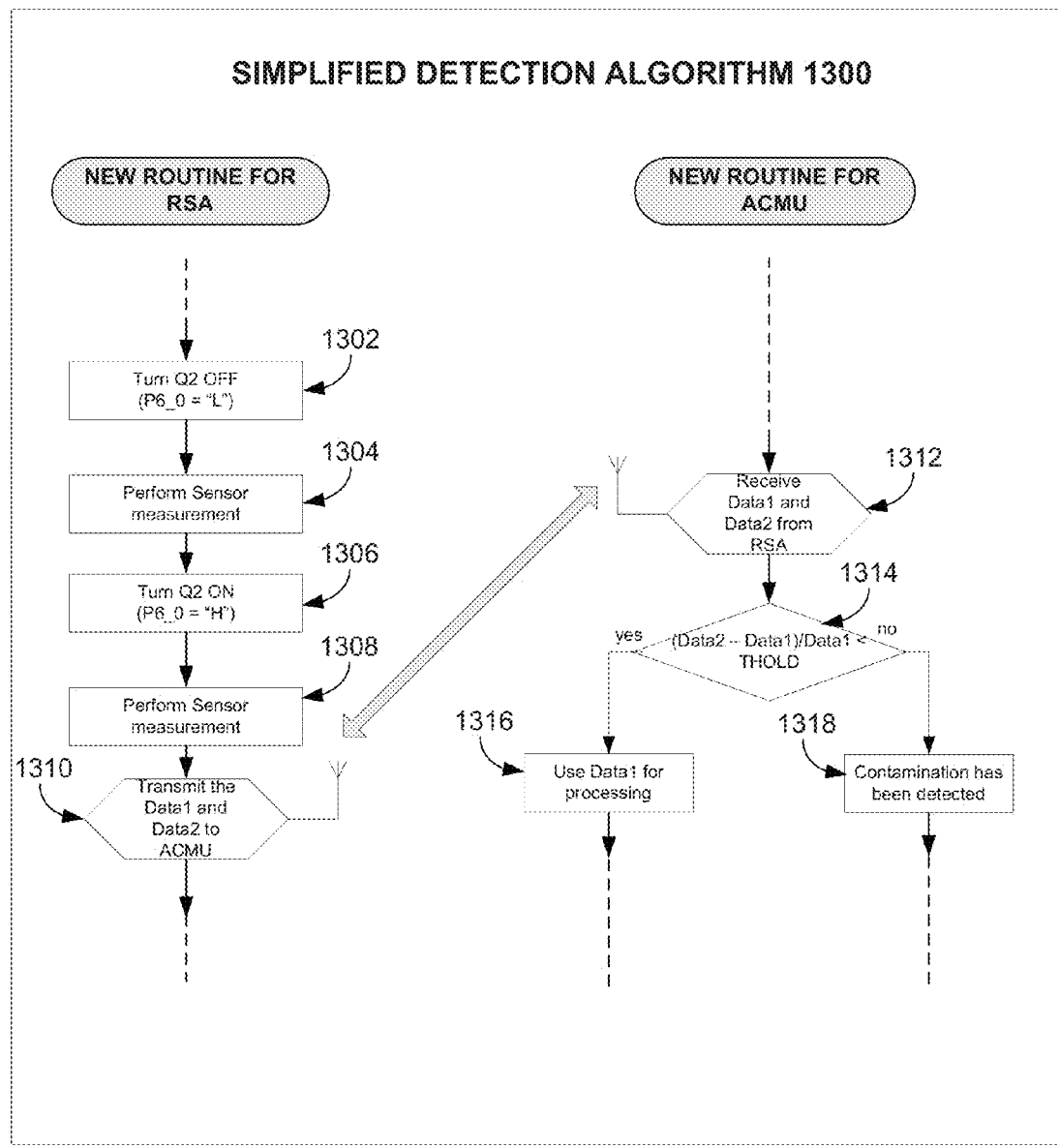
FIG. 13 illustrates a first detection algorithm in accordance with various aspects.
Figure 14:
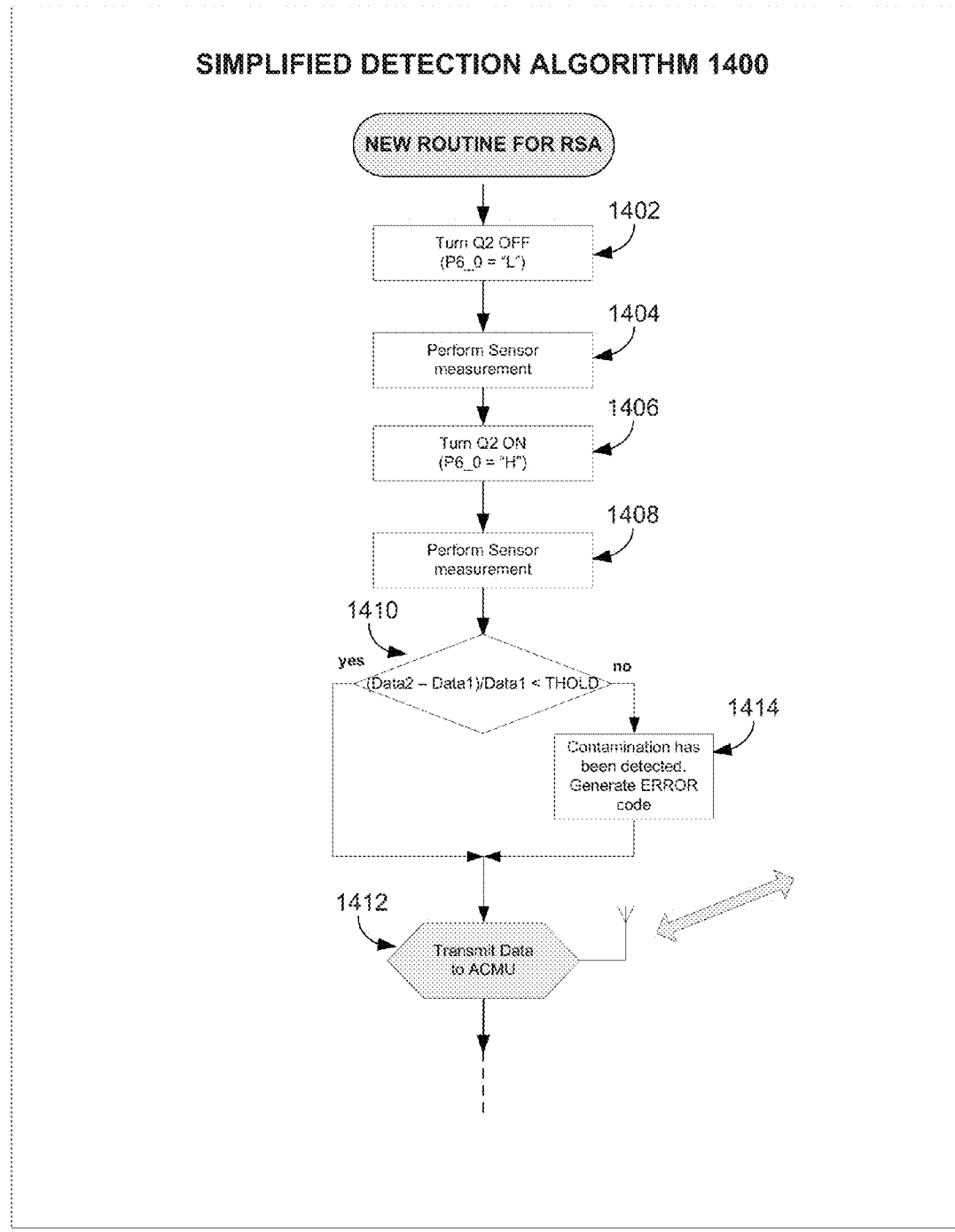
FIG. 14 illustrates a second detection algorithm in accordance with various aspects.

Based on the simulations, the detection algorithms shown in FIGS. 13 and 14 are proposed. FIGS. 13 and 14 refer to components of the RSA 900 as shown in FIGS. 9 and 10.

FIG. 13 shows a detection algorithm 1300. At block 1302, Q2 is turned off, thereby placing the RSA in the measurement mode. If Q2 is already turned off, block 1302 may be omitted. A sensor measurement is then performed at block 1304 to obtain a first value of the sensor signal received by the RSA during the measurement mode. At block 1306, Q2 is turned on, thereby placing the RSA in the detection mode. A sensor measurement is then performed at block 1308 to obtain a second value of the sensor signal received by the RSA during the detection mode.

At block 1310, the first and second values (Data1 and Data2, respectively) are transmitted to a monitoring unit. The monitoring unit receives the first and second values at block 1312. At block 1314, the monitoring unit compares the first value with the second value according to the formula (Data2−Data1)/Data1. The monitoring unit compares this quantity to a threshold (THOLD).

TABLE 2

| Sensor Resistance (MΩ) | Sensor Current (nA) | Contamination Resistance (MΩ) | Simulation OA output (mV) | | | | % OF CHANGE | |
|---|---|---|---|---|---|---|---|---|
| | | | @ +150 uV difference | | @ −150 uV difference | | @ +150 uV difference | @ −150 uV difference |
| | | | Q2 = OFF | Q2 = ON | Q2 = OFF | Q2 = ON | | |
| 5.42 | 120 | 0.1 | 1860 | 3300 | 1840 | 3300 | 77% | 79% |
| | | 1.0 | 1850 | 3300 | 1850 | 3300 | 78% | 78% |
| | | 5.0 | 1850 | 3300 | 1850 | 3140 | 78% | 70% |
| | | 10.0 | 1850 | 2500 | 1850 | 2500 | 35% | 35% |
| | | 100.0 | 1850 | 1910 | 1850 | 1910 | 3% | 3% |
| 10.83 | 60 | 0.1 | 1260 | 3300 | 1240 | 3300 | 162% | 166% |
| | | 1.0 | 1250 | 3300 | 1250 | 3300 | 164% | 164% |
| | | 5.0 | 1250 | 2540 | 1250 | 3300 | 103% | 164% |
| | | 10.0 | 1250 | 1900 | 1250 | 1900 | 52% | 52% |
| | | 100.0 | 1250 | 1310 | 1250 | 1310 | 5% | 5% |
| 100 | 6.5 | 1.0 | 724.54 | 3300 | 709.27 | 3300 | 355% | 365% |
| | | 5.0 | 715.48 | 2010 | 714.71 | 2100 | 181% | 194% |
| | | 10.0 | 715.25 | 1360 | 714.85 | 1360 | 90% | 90% |
| | | 100.0 | 715.02 | 779.6 | 714.99 | 779.6 | 9% | 9% |
| 20,000 (20 GΩ) | 0.325 (325 pA) | 0.1 | 659.87 | 3300 | 644.6 | 3300 | 400% | 412% |
| | | 1.0 | 652.48 | 3300 | 649.03 | 3300 | 406% | 408% |
| | | 5.0 | 650.81 | 1940 | 650.03 | 1940 | 198% | 198% |
| | | 10.0 | 650.57 | 1300 | 650.18 | 1300 | 100% | 100% |
| | | 100.0 | 650.31 | 714.93 | 650.31 | 714.93 | 10% | 10% |

Additionally, FIGS. 12A-D show graphs that demonstrate how the transimpedance amplifier output voltage swings when MOSFET Q2 switches ON/OFF (thereby switching between detection mode and measurement mode, respec- If the calculated quantity is less than the threshold, the monitoring unit uses Data1 for processing at block 1316 (e.g., for determining the glucose level of the patient). However, if the calculated quantity is greater than the threshold, the monitoring unit determines that contamination is present on the RSA contacts at block 1318. The monitoring unit initiates one or more actions in response to the finding of contamination, such as activating an alarm and/or excluding Data1 from being used for processing. In an aspect, data sets Data1 and/or Data2 may include additional values in addition the first value and second value, respectively. The additional data may be used for detection purposes, and/or for sensor measurement purposes.

In an aspect, the value of the threshold (e.g., the actual maximum allowable difference between the first and second values) may be determined based on tests with real contamination substances.

FIG. 14 illustrates a method 1400 in which the RSA performs the comparison between the first value and the second value, rather than the monitoring unit. Blocks 1402, 1404, 1406, and 1408 are similar to blocks 1302, 1304, 1306, and 1308, respectively, as discussed above. At block 1410, the RSA compares the first value to the second value and compares this quantity against a threshold. If the results of the comparison are less than the threshold, the RSA transmits the data to the monitoring unit at block 1412. In an aspect, the RSA only transmits Data1. Alternatively, the RSA may transmit Data2 and/or information related to the results of the detection algorithm 1400 in addition to Data1.

If the results of the comparison are greater than the threshold, the RSA determines, at block 1414, that contamination is present that is causing a leakage current. In response, the RSA generates an error code. The RSA transmits, at block 1412, data to the monitoring unit. The transmitted data may include Data1, Data2, the error code, and/or other information regarding the algorithm 1400. In an aspect, Data1 may not be transmitted to the monitoring unit if the results of the comparison are greater than the threshold.

The monitoring unit may include any suitable structure for communicating with the RSA, processing the data received from the RSA, and/or presenting information to the patient and/or a caregiver. For example, the monitoring unit may be a computing device, such as a personal data assistant, mobile phone, personal computer, laptop computer, tablet computer, and/or a dedicated computing device for the sensor system.

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

What is claimed is:
1. An electronics assembly comprising:
a hermetic housing;
a sensor contact disposed on an exterior surface of the housing, and configured to receive a sensor signal from a sensor assembly when the sensor assembly is coupled to the electronics assembly, the sensor signal being representative of a level of an analyte in a body;
a processor coupled to the sensor contact and configured to receive the sensor signal;
an open detection contact disposed on the exterior surface of the housing that is not couplable to any contact on the sensor assembly and is configured to detect a leakage current between the sensor contact and the open detection contact due to contamination at or near the sensor contact; and
a switch coupled to the detection contact, controlled by the processor, and configured to couple the detection contact to a bias voltage during a measurement mode and to couple the detection contact to a reference voltage during a detection mode, the reference voltage being different from the bias voltage,
wherein the processor is configured to periodically switch from the measurement mode to the detection mode and measure a first value of the sensor signal during the measurement mode and a second value of the sensor signal during the detection mode to detect a leakage current of the sensor signal, wherein if the difference between the first value and the second value is greater than a threshold amount, the processor identifies that there is a leakage current present.

2. The electronics assembly of claim 1, wherein the processor is configured to compare the first value to the second value to determine whether the leakage current is present.

3. The electronics assembly of claim 2, wherein the electronics assembly is further configured to take an action based on the comparison of the first value to the second value, the action including at least one of: activating an alarm, generating an error code, transmitting the error code to an external device, logging an error, stopping collection of data from the sensor assembly, preventing the sensor data from being used in data processing, and/or taking the leakage current into account in data processing.

4. The electronics assembly of claim 2, wherein the processor is configured to take an action if a result of the comparison between the first value and the second value is above a threshold.

5. The electronics assembly of claim 1, wherein the processor is configured to transmit the first and second values to a monitoring unit, the monitoring unit configured to determine whether the leakage current is present based on the first and second values.

6. The electronics assembly of claim 1, further comprising:
a transimpedance amplifier configured to receive the sensor signal at an input terminal and to pass an amplified sensor signal to the processor, the amplified sensor signal having a voltage dependent on a current of the sensor signal at the input terminal; wherein the transimpedance amplifier is biased with the bias voltage.

7. The electronics assembly of claim 1, further comprising a battery, wherein the detection contact is configured to be coupled with a battery charger to charge the battery during a charging mode of the electronics assembly.

8. The electronics assembly of claim 7, wherein the switch comprises a first switch and the electronics assembly further comprising:
a second switch configured to couple the detection contact to the battery during the charging mode and to couple the detection contact to the first switch during the measurement mode and the detection mode.

9. The electronics assembly of claim 8, further comprising an enable contact configured to receive a control signal from the battery charger to place the electronics assembly in the charging mode.

10. The electronics assembly of claim 1, further comprising a common return contact coupled to a ground potential and configured to be coupled with the sensor assembly.

11. The electronics assembly of claim 10, wherein the reference voltage is equal to the ground potential.

12. The electronics assembly of claim 10, wherein the sensor contact, detection contact, and the common return contact are disposed in a sealed portion between the electronics assembly and the sensor assembly when the electronics assembly is coupled with the sensor assembly.

13. The electronics assembly of claim 1, wherein the detection contact comprises a guard ring that surrounds the sensor contact.

14. The electronics assembly of claim 1, wherein the sensor assembly includes a continuous glucose monitor configured to produce the sensor signal.

15. An analyte sensor system, comprising:
a sensor assembly including:
a first sensor contact;
a first ground contact; and
an analyte sensor coupled to the first sensor contact and the first ground contact, the analyte sensor configured to produce a sensor signal at the first sensor contact that is representative of a level of an analyte in a body; and
an electronics assembly that reversibly couples to the sensor assembly, the electronics assembly including:
a hermetic housing
a second sensor contact disposed on an exterior surface of the housing and configured to be coupled with the first sensor contact to receive the sensor signal;
a second ground contact disposed on the exterior surface of the housing and coupled to the first ground contact and to a ground potential;
a processor coupled to the second sensor contact and configured to receive the sensor signal;
an open detection contact disposed on the exterior surface of the housing that is not couplable to any contact of the sensor assembly and is configured to detect a leakage current between the sensor contact and the open detection contact due to contamination at or near the sensor contact; and
a switch coupled to the detection contact and controlled by the processor, the switch configured to couple the detection contact to a bias voltage during a measurement mode and to couple the detection contact to a reference voltage during a detection mode, the reference voltage being different from the bias voltage, wherein the processor is configured to periodically switch from the measurement mode to the detection mode and measure a first value of the sensor signal during the measurement mode and a second value of the sensor signal during the detection mode to detect a leakage current of the sensor signal, wherein if the difference between the first value and the second value is greater than a threshold amount, the processor identifies that there is a leakage current present.

16. The system of claim 15, wherein the processor is configured to compare the first value to the second value to determine whether the leakage current is present, and to take an action if a result of the comparison is above a threshold.

17. The system of claim 15, wherein the electronics assembly further comprises a transimpedance amplifier configured to receive the sensor signal at an input terminal and to pass an amplified sensor signal to the processor, wherein the transimpedance amplifier is biased with the bias voltage.

18. The system of claim 15, wherein the electronics assembly further comprises a battery, and wherein the detection contact is configured to be coupled with a battery charger to charge the battery during a charging mode of the electronics assembly.

19. The system of claim 18, wherein the electronics assembly further comprises an enable contact configured to receive a control signal from the battery charger to place the electronics assembly in the charging mode.

20. The system of claim 18, wherein the reference voltage is equal to the ground potential.

21. The system of claim 15, wherein the first and second sensor contacts, first and second ground contacts, and the detection contact are disposed in a sealed portion between the electronics assembly housing and the sensor assembly when the electronics assembly and the sensor assembly are coupled.

22. The system of claim 15, wherein the detection contact comprises a guard ring that surrounds the second sensor contact.

23. The system of claim 15, wherein the analyte sensor includes a continuous glucose monitor.

* * * * *